United States Patent
Allen et al.

(10) Patent No.: US 9,249,373 B2
(45) Date of Patent: Feb. 2, 2016

(54) LAUNDRY DETERGENTS BASED ON COMPOSITIONS DERIVED FROM NATURAL OIL METATHESIS

(75) Inventors: Dave R. Allen, Chicago, IL (US); Marcos Alonso, Chicago, IL (US); Randal J. Bernhardt, Antioch, IL (US); Dennis S. Murphy, Libertyville, IL (US); Patrick Shane Wolfe, Palatine, IL (US); Aaron Brown, Chicago, IL (US)

(73) Assignee: Stepan Company, Northfield, IL (US)

( * ) Notice: Subject to any disclaimer, the term of this patent is extended or adjusted under 35 U.S.C. 154(b) by 179 days.

(21) Appl. No.: 13/880,024

(22) PCT Filed: Oct. 25, 2011

(86) PCT No.: PCT/US2011/057622
§ 371 (c)(1),
(2), (4) Date: May 13, 2013

(87) PCT Pub. No.: WO2011/057622
PCT Pub. Date: May 10, 2012

(65) Prior Publication Data
US 2013/0217608 A1    Aug. 22, 2013

Related U.S. Application Data

(60) Provisional application No. 61/406,570, filed on Oct. 25, 2010, provisional application No. 61/406,547, filed on Oct. 25, 2010, provisional application No. 61/406,556, filed on Oct. 25, 2010.

(51) Int. Cl.
C11D 1/12 (2006.01)
C11D 1/28 (2006.01)
C11D 1/62 (2006.01)
C11D 1/75 (2006.01)
(Continued)

(52) U.S. Cl.
CPC . *C11C 3/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01); *C08K 5/20* (2013.01); *C09K 8/00* (2013.01); *C09K 15/28* (2013.01); *C11C 3/00* (2013.01); *C11D 1/002* (2013.01); *C11D 1/04* (2013.01); *C11D 1/28* (2013.01); *C11D 1/62* (2013.01); *C11D 1/652* (2013.01); *C11D 1/72* (2013.01); *C11D 1/74* (2013.01); *C11D 1/83* (2013.01); *C11D 1/86* (2013.01); *C11D 1/90* (2013.01); *C11D 1/92* (2013.01); *C11D 1/94* (2013.01); *C11D 3/48* (2013.01)

(58) Field of Classification Search
CPC .............. C11D 1/28; C11D 1/72; C11D 1/83; C11D 1/88; C11D 1/94; C11D 3/30; C11D 3/32; C11D 1/143; C11D 1/18; C11D 1/90; C11D 3/3463; C11D 3/3472; C11D 3/349
USPC ......... 510/350, 351, 356, 500, 505, 506, 492, 510/494, 495, 501, 503
See application file for complete search history.

(56) References Cited

U.S. PATENT DOCUMENTS 2,653,970 A   9/1953   Fessler et al.
3,169,142 A   2/1965   Knaggs et al.
(Continued)

FOREIGN PATENT DOCUMENTS

WO   WO-2008048522   4/2008

OTHER PUBLICATIONS

Tetrahedron 68 2012, 1117.
Appl. Catal.A. 346 2009, 158.
J.C. Mol., Topics in Catalysis 27 2004, 97.
J. C. Mol., Green Chem., Apr. 2002, 5.

*Primary Examiner* — Gregory R Delcotto
(74) *Attorney, Agent, or Firm* — Dilworth IP LLC

(57) ABSTRACT

Laundry detergents useful for cold-water cleaning and boosted bargain detergents are disclosed. The detergents include a surfactant composition derived from a metathesis-derived $C_{10}$-$C_{17}$ monounsaturated acid, octadecene-1,18-dioic acid, or their ester derivatives. For fatty alkyl ester sulfonate-containing detergents, the composition is selected from $C_{10}$ betaines, $C_{12}$ or $C_{16}$ amidoamines, $C_{12}$ ethanolamine amides, $C_{16}$ amidoamine sulfonates, $C_{18}$ diamidoamine dioxides, quaternized $C_{18}$ diamidoamine betaines, sulfonated $C_{18}$ low-EO fatty ester alkoxylates, $C_{18}$ amidoamine carboxylates, and amidoamine oxides and sulfobetaines derived from cross-metathesis of palm or soybean oil. The bargain detergents include a performance booster selected from $C_{12}$ low-EO fatty ester alkoxylate sulfonates, $C_{18}$ amidoamine oxide esters, $C_{18}$ amidoamine oxide carboxylates, and amidoamine sulfobetaines made from self metathesized palm or soybean oil.

7 Claims, No Drawings

(51) Int. Cl.

| | | |
|---|---|---|
| C11C 3/08 | (2006.01) | |
| C11D 1/72 | (2006.01) | |
| A01N 25/02 | (2006.01) | |
| A01N 25/04 | (2006.01) | |
| A01N 25/30 | (2006.01) | |
| A01N 33/12 | (2006.01) | |
| A01N 37/18 | (2006.01) | |
| A01N 37/44 | (2006.01) | |
| A01N 41/04 | (2006.01) | |
| A61K 8/41 | (2006.01) | |
| A61K 8/42 | (2006.01) | |
| A61K 8/44 | (2006.01) | |
| A61K 8/46 | (2006.01) | |
| A61K 8/92 | (2006.01) | |
| A61Q 5/12 | (2006.01) | |
| A61Q 19/10 | (2006.01) | |
| A62D 1/02 | (2006.01) | |
| B01F 17/00 | (2006.01) | |
| C07C 69/533 | (2006.01) | |
| C07C 69/593 | (2006.01) | |
| C07C 209/12 | (2006.01) | |
| C07C 211/21 | (2006.01) | |
| C07C 219/08 | (2006.01) | |
| C07C 231/12 | (2006.01) | |
| C07C 237/16 | (2006.01) | |
| C07C 303/18 | (2006.01) | |
| C08G 65/26 | (2006.01) | |
| C08K 5/01 | (2006.01) | |
| C08K 5/20 | (2006.01) | |
| C09K 8/00 | (2006.01) | |
| C09K 15/28 | (2006.01) | |
| C11C 3/00 | (2006.01) | |
| C11D 1/00 | (2006.01) | |
| C11D 1/04 | (2006.01) | |
| C11D 1/65 | (2006.01) | |
| C11D 1/74 | (2006.01) | |
| C11D 1/83 | (2006.01) | |
| C11D 1/90 | (2006.01) | |
| C11D 1/92 | (2006.01) | |
| C11D 1/94 | (2006.01) | |
| C11D 3/48 | (2006.01) | |
| C11D 1/86 | (2006.01) | |

(56) References Cited

U.S. PATENT DOCUMENTS

| | | | |
|---|---|---|---|
| 3,544,613 A | | 12/1970 | Knaggs et al. |
| 3,630,929 A | | 12/1971 | van Dijk |
| 3,929,678 A | | 12/1975 | Laughlin et al. |
| 4,087,457 A | | 5/1978 | Convers et al. |
| 4,148,821 A | | 4/1979 | Nussbaum et al. |
| 4,248,729 A | | 2/1981 | Rubingh et al. |
| 4,275,013 A | | 6/1981 | Tokosh et al. |
| 4,316,812 A | | 2/1982 | Hancock et al. |
| 4,359,413 A | | 11/1982 | Ward et al. |
| 4,397,776 A | | 8/1983 | Ward |
| 4,545,941 A | | 10/1985 | Rosenburg |
| 4,758,376 A | * | 7/1988 | Hirota et al. .............. 510/467 |
| 5,211,883 A | * | 5/1993 | Yamashina et al. ........ 510/121 |
| 5,478,500 A | | 12/1995 | Swift et al. |
| 5,482,908 A | | 1/1996 | Le-khac |
| 5,556,615 A | * | 9/1996 | Janchitraponvej et al. 424/70.11 |
| 5,587,500 A | | 12/1996 | Hovda |
| 5,723,533 A | | 3/1998 | Lawson et al. |
| 5,929,022 A | | 7/1999 | Velazquez |
| 5,945,394 A | | 8/1999 | Sajic et al. |
| 5,965,508 A | | 10/1999 | Ospinal et al. |
| 6,058,623 A | | 5/2000 | Brooks et al. |
| 6,239,093 B1 | * | 5/2001 | Foley et al. .................. 510/352 |
| 6,399,553 B1 | | 6/2002 | Cable et al. |
| 6,489,285 B2 | | 12/2002 | Faber |
| 6,511,953 B1 | | 1/2003 | Fontana et al. |
| 6,660,706 B1 | | 12/2003 | Koester et al. |
| 6,949,498 B2 | | 9/2005 | Murphy et al. |
| 7,078,373 B2 | | 7/2006 | Burrows et al. |
| 7,098,175 B2 | | 8/2006 | Hsu et al. |
| 7,205,268 B2 | | 4/2007 | Hsu et al. |
| 7,244,698 B2 | * | 7/2007 | Treybig et al. .............. 510/188 |
| 7,291,582 B2 | | 11/2007 | Hsu et al. |
| 7,517,842 B2 | * | 4/2009 | Barnhart et al. ............. 510/138 |
| 7,576,227 B2 | | 8/2009 | Bicerano et al. |
| 7,608,573 B1 | | 10/2009 | Scheuing et al. |
| 7,635,393 B2 | | 12/2009 | Hsu |
| 7,718,816 B2 | * | 5/2010 | Yajima et al. ................ 554/35 |
| 7,820,612 B2 | | 10/2010 | English, III |
| 7,960,599 B2 | | 6/2011 | Millis et al. |
| 8,067,610 B2 | | 11/2011 | Schrodi |
| 2002/0187909 A1 | | 12/2002 | Gupta et al. |
| 2003/0171244 A1 | | 9/2003 | Schmid et al. |
| 2007/0010680 A1 | * | 1/2007 | Yajima et al. ................ 554/51 |
| 2008/0009430 A1 | | 1/2008 | Hecht et al. |
| 2008/0033026 A1 | | 2/2008 | Zullo et al. |
| 2008/0139434 A1 | * | 6/2008 | Basappa et al. .............. 510/159 |
| 2008/0280805 A1 | | 11/2008 | English, III et al. |
| 2009/0264672 A1 | | 10/2009 | Abraham et al. |
| 2010/0016198 A1 | | 1/2010 | Bernhardt et al. |
| 2010/0120658 A1 | * | 5/2010 | Schiedel et al. .............. 510/515 |
| 2010/0145086 A1 | | 6/2010 | Schrodi et al. |
| 2010/0282467 A1 | | 11/2010 | Hutchison et al. |
| 2011/0113679 A1 | | 5/2011 | Cohen et al. |
| 2011/0313180 A1 | | 12/2011 | Uptain et al. |
| 2012/0071676 A1 | | 3/2012 | Schrodi et al. |
| 2012/0197031 A1 | | 8/2012 | Firth et al. |
| 2013/0035502 A1 | | 2/2013 | Cohen et al. |
| 2013/0035532 A1 | | 2/2013 | Schrodi |

* cited by examiner

LAUNDRY DETERGENTS BASED ON COMPOSITIONS DERIVED FROM NATURAL OIL METATHESIS

FIELD OF THE INVENTION

The invention relates to compositions derived from natural oil metathesis and useful in laundry detergents, particularly detergents useful for cold-water cleaning and boosted bargain detergents.

BACKGROUND OF THE INVENTION

Modern laundry detergents must meet demanding requirements: the ability to clean all kinds of greasy, oily dirt, grass stains; usefulness in cold water; good biodegradability; low environmental impact; ability to be formulated in a highly concentrated formulation while maintaining good solubility and storage stability. Liquid laundry detergents usually include one or more anionic surfactants, nonionic surfactants, water, and other additives including alkalinity agents, builders, fragrances, enzymes, and other components.

The surfactant system used in an economical detergent formulation ("bargain detergent") may comprise only an anionic surfactant, typically a neutralized alkylbenzene sulfonic acid, and a nonionic surfactant, often an alcohol ethoxylate, as the surfactant components. While this system provides acceptable performance across a wide range of soils and stains, adding a third surfactant can be included to boost performance. The challenge is to find a surfactant, useful at an additive level (e.g., 1 wt. % actives), that improves performance without taking too big of a bite out of the budget. Alkyl ether sulfates and fatty amine oxides (e.g., lauramine oxide), are often used as detergent boosters (see U.S. Pat. Nos. 7,078,373; 4,248,729; 4,359,413; and 4,397,776).

Laundry detergents that include fatty alkyl ester sulfonates, particularly lower alkyl ester sulfonates from $C_{12}$-$C_{20}$ fatty acids, and especially $C_{16}$ methyl ester sulfonates, provide good cold-water cleaning performance (see, e.g., U.S. Pat. No. 7,820,612 and U.S. Pat. Appl. Publ. Nos. 2008/0009430 and 2010/0016198). One issue with methyl ester sulfonates (hereinafter "MES") is solubility, particularly for the highly concentrated detergent formulations now commonly sold. The MES-based formulations can display undesirable changes in product form due to lack of physical stability, for example by gelling or becoming cloudy due to precipitation. To counteract the solubility issue, an additional surfactant, often a nonionic surfactant such as cocamide DEA, is included with the MES. This solution is only partially satisfactory, however, because although the nonionic surfactant helps to stabilize the MES-based detergent at room temperature, precipitates can develop upon long-term storage or exposure to low temperatures. It would therefore be helpful to identify other surfactants that can improve the solubility of MES-based detergents as well as or better than cocamide DEA.

Occasionally, laundry detergents have been formulated to include fatty esters or amides made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. These materials are generally less than completely satisfactory, however, because compounds having such large carbon chains can behave functionally as soil under some laundering conditions.

Recent improvements in metathesis catalysts (see J. C. Mol, Green Chem. 4 (2002) 5) provide an opportunity to generate reduced chain length, monounsaturated feedstocks, which are valuable for making detergents and surfactants, from $C_{16}$ to $O_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, surfactants have generally not been made from these feedstocks.

We recently described new compositions made from feedstocks based on self-metathesis of natural oils or cross-metathesis of natural oils and olefins. In particular, we identified esteramines and ester quats, fatty amides, fatty amines and amidoamines, quaternized amines, betaines, sulfobetaines, alkoxylates, sulfonates, sulfo-estolides, and other compositions made by derivatizing the unique feedstocks (see copending PCT/US11/57596, PCT/US11/57597, PCT/US11/57595, PCT/US11/57602, PCT/US11/57605, PCT/US11/57609, all filed Oct. 25, 2011. The feedstocks, which include metathesis-derived $C_{10}$-$C_{17}$ monounsaturated acids, octadecene-1,18-dioic acid, and their ester derivatives, preferably have at least 1 mole % of trans-$\Delta^9$ unsaturation. Because performance of a particular surfactant or blend of surfactants as an MES solubilizer, cold-water cleaning additive, or booster for bargain laundry detergents is not easily inferred from surfactant structure, we performed extensive experimental investigations to identify subclasses of surfactants having desirable performance in these areas.

New surfactant classes are always of interest to formulators of laundry detergents. Surfactants based on renewable resources will continue to be in demand as alternatives to petroleum-based surfactants. Traditional natural sources of fatty acids and esters used for making surfactants generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). Formulators will benefit from identification of particular subclasses of surfactants that derive from renewable sources and have desirable attributes for use in laundry detergents.

SUMMARY OF THE INVENTION

In one aspect, the invention relates to a laundry detergent useful for cold-water cleaning. This detergent comprises an anionic surfactant, a nonionic surfactant, a fatty alkyl ester sulfonate, and a surfactant composition derived from a metathesis-derived $C_{10}$-$C_{17}$ monounsaturated acid, octadecene-1,18-dioic acid, or their ester derivatives. The metathesis-derived surfactant composition is selected from $C_{10}$ betaines, $C_{12}$ or $C_{16}$ amidoamines, $C_{12}$ ethanolamine amides, $C_{16}$ amidoamine sulfonates, $C_{18}$ diamidoamine dioxides, quaternized $C_{18}$ diamidoamine betaines, sulfonated $C_{18}$ low-EO fatty ester alkoxylates, $C_{18}$ amidoamine carboxylates, and amidoamine oxides and sulfobetaines derived from cross-metathesis of palm or soybean oil.

The invention includes a boosted bargain laundry detergent. This detergent comprises an anionic surfactant, a nonionic surfactant, and a performance booster derived from a metathesis-derived $C_{10}$-$C_{17}$ monounsaturated acid, octadecene-1,18-dioic acid, or their ester derivatives and selected from the group consisting of $C_{12}$ low-EO fatty ester alkoxylate sulfonates, $C_{18}$ amidoamine oxide esters, $C_{18}$ amidoamine oxide carboxylates, and amidoamine sulfobetaines made from self-metathesized palm or soybean oil.

The inventive compositions can take many forms, including liquid, powder, paste, granule, tablet, molded solid, water-soluble sheet, or water-soluble sachet. We surprisingly found that the particular classes of surfactant compositions and performance boosters identified above, all derived from renewable resources, rival or outperform commercial standards when tested as either a complement to an alkyl ester sulfonate for cold-water detergents or as a booster for a bargain detergent formula.

DETAILED DESCRIPTION OF THE INVENTION

Detergent compositions useful for cold-water cleaning comprise an anionic surfactant, a nonionic surfactant, a fatty alkyl ester sulfonate, and a surfactant composition derived from a metathesis-derived $C_{10}$-$C_{17}$ monounsaturated acid, octadecene-1,18-dioic acid, or their ester derivatives. The metathesis-derived surfactant composition is selected from $C_{10}$ betaines, $C_{12}$ or $C_{16}$ amidoamines, $C_{12}$ ethanolamine amides, $C_{16}$ amidoamine sulfonates, $C_{18}$ diamidoamine dioxides, quaternized $C_{18}$ diamidoamine betaines, sulfonated $C_{18}$ low-EO fatty ester alkoxylates, $C_{18}$ amidoamine carboxylates, and amidoamine oxides and sulfobetaines derived from cross-metathesis of palm or soybean oil.

The detergent composition can take any of a number of forms. For example, it can be an isotropic liquid, a surfactant-structured liquid, a granular, spray-dried or dry-blended powder, a tablet, a paste, a molded solid, or any other laundry detergent form known to those skilled in the art. Water soluble sheets or sachets, such as those described in U.S. Pat. Appl. Publ. No. 2002/0187909, which is incorporated herein by reference, are also suitable.

Suitable anionic surfactants are well known in the art. Anionic surfactants generally have a molecular weight below 10,000 and comprise one or more functional groups that exhibit a net anionic charge when in aqueous solution at the normal wash pH, which typically ranges from 6 to 11. Suitable anionic surfactants include $C_4$-$C_{30}$ carboxylates, fatty alkyl sulfates (alcohol sulfates, "AS"), fatty alkyl ether sulfates (alcohol ether sulfates, "AES"), paraffin sulfonates, olefin sulfonates, alkyl aryl sulfonates (e.g., linear alkylbenzene sulfonates, "LAS"), fatty ester sulfonates, sulfosuccinate esters, organic phosphates, and the like. Preferred anionic surfactants include alkylbenzene sulfonates having a linear $C_8$-$C_{18}$ alkyl group, more preferably a linear $C_{11}$-$C_{14}$ alkyl group; primary fatty alkyl sulfates and fatty alkyl ether sulfates derived from $C_8$-$C_{18}$ alcohols; $C_8$-$C_{22}$ paraffin sulfonates; and $C_8$-$C_{22}$ olefin sulfonates. The carboxylate, phosphate, sulfate, and sulfonate salts usually have a monovalent counterion, e.g., an alkali metal, ammonium, or quaternary nitrogen ion. Linear alkylbenzene sulfonates are particularly preferred. Additional examples of suitable anionic surfactants are described in U.S. Pat. Nos. 3,929,678; 5,929,022; 6,399,553; 6,489,285; 6,511,953; 6,949,498; 7,098,175; and U.S. Pat. Appl. Publ. No. 2010/0016198 (see especially pp. 11-13), the teachings of which are incorporated herein by reference. The amount of anionic surfactant can range from 1 to 70 wt. %, more preferably from 2 to 60 wt. %, and most preferably from 5 to 40 wt. % of the formulation.

Suitable nonionic surfactants are also well known. Nonionic surfactants are neutral and comprise a hydrophobic group and an organic hydrophilic group. Conveniently, the hydrophilic group comprises one or more recurring units derived from ethylene oxide, and the hydrophilic/lipophilic balance of the nonionic surfactant is adjusted to the desired level by controlling the proportion of ethylene oxide used. Suitable nonionic surfactants include fatty alcohols, fatty alcohol alkoxylates, alkylphenol alkoxylates, ether-capped fatty alcohol alkoxylates, alkoxylated fatty esters, alkoxylate block copolymers, alkylpolysaccharides, alkoxylated fatty amides, polyhydroxy fatty amides, fatty amine oxides, castor oil alkoxylates, polyol esters, glycerol esters, glycol fatty esters, tallow amine ethoxylates, and the like. Particularly preferred are $C_{12}$-$C_{18}$ alkyl ethoxylates, especially $C_{12}$-$C_{15}$ primary alcohol ethoxylates having from 6 to 9 moles of ethylene oxide recurring units. Additional examples of suitable nonionic surfactants are described in U.S. Pat. Nos. 3,630,929; 4,316,812; 5,929,022; 7,098,175; and U.S. Pat. Appl. Publ. No. 2010/0016198 (see especially pp. 14-15), the teachings of which are incorporated herein by reference. The amount of nonionic surfactant can range from 5 to 70 wt. %, more preferably from 10 to 50 wt. %, and most preferably from 15 to 40 wt. % of the formulation.

The detergents for cold-water cleaning preferably include water. Typically, the amount of water ranges from 30 to 80 wt. %, more preferably from 40 to 70 wt. %, and most preferably from 50 to 60 wt. %. In one aspect, the detergent is a storage-stable liquid at 20° C. Preferably, such storage-stable liquids exhibit a phase transition below 5° C. Preferably, the liquid detergent resists forming precipitates and remains homogeneous upon prolonged storage, e.g., for months at a time.

The detergents for cold-water cleaning also comprise a fatty alkyl ester sulfonate, preferably a sulfonate of a methyl ester of a $C_{12}$-$C_{20}$ fatty acid, more preferably a $C_{14}$-$C_{16}$ methyl ester sulfonate, and most preferably a $C_{16}$ methyl ester sulfonate. The fatty alkyl ester sulfonate provides good cold-water cleaning performance (see, e.g., U.S. Pat. No. 7,820,612 and U.S. Pat. Appl. Publ. Nos. 2008/0009430 and 2010/0016198). Processes for making fatty alkyl ester sulfonates are well known (see, e.g., U.S. Pat. Nos. 5,587,500; 5,723,533; and 6,058,623, the teachings of which are incorporated herein by reference). Methyl esters obtained from natural oils are usually sulfonated at the carbon alpha to the carbonyl, followed by digestion to ensure optimal conversion to the fatty alkyl ester sulfonate. Bleaching and neutralization steps generally follow. Typically, the amount of fatty alkyl ester sulfonate in the detergent ranges from 3 to 25 wt. %, more preferably from 5 to 15 wt. %, and most preferably from 8 to 12 wt. %.

The detergents for cold-water cleaning further comprise a surfactant composition derived from a metathesis-derived $C_{10}$-$C_{17}$ monounsaturated acid, octadecene-1,18-dioic acid, or their ester derivatives. The composition is selected from $C_{10}$ betaines, $C_{12}$ or $C_{16}$ amidoamines, $C_{12}$ ethanolamine amides, $C_{16}$ amidoamine sulfonates, $C_{18}$ diamidoamine dioxides, quaternized $C_{18}$ diamidoamine betaines, sulfonated $C_{18}$ low-EO fatty ester alkoxylates, $C_{18}$ amidoamine carboxylates, and amidoamine oxides and sulfobetaines derived from cross-metathesis of palm or soybean oil. Further details of these compositions will be described later. The composition is preferably used in an amount within the range of 0.5 to 10 wt. %, more preferably from 1 to 8 wt. %, most preferably from 2 to 6 wt. % based on the total amount of detergent.

In another aspect, the invention relates to a boosted bargain laundry detergent. The boosted bargain detergent comprises an anionic surfactant, a nonionic surfactant, and a performance booster. Suitable anionic and nonionic surfactants have already been described. The boosted bargain detergent does not normally include the fatty alkyl ester sulfonate (MES) component described above for use in the detergent for cold-water cleaning. Instead, it relies on a third surfactant (a "booster") that can be used at an additive level (e.g., 1 wt. % actives) to improve performance while preserving a low cost position.

The performance booster is derived from a metathesis-derived $C_{10}$-$C_{17}$ monounsaturated acid, octadecene-1,18-dioic acid, or their ester derivatives. The booster is selected from $C_{12}$ low-EO fatty ester alkoxylate sulfonates, $C_{18}$ amidoamine oxide esters, $C_{18}$ amidoamine oxide carboxylates, and amidoamine sulfobetaines made from self-metathesized palm or soybean oil. The booster is preferably used in the bargain detergent an amount within the range of 0.1 to 5 wt. %, more preferably from 0.2 to 4 wt. %, most preferably from 0.5 to 2 wt. % based on the total amount of detergent.

The amount of anionic surfactant in the boosted bargain detergent can range from 1 to 70 wt. %, more preferably from 2 to 60 wt. %, and most preferably from 5 to 40 wt. % of the formulation. The boosted bargain detergent preferably comprises the nonionic surfactant in an amount within the range of 5 to 70 wt. %, more preferably from to 50 wt. %, and most preferably from 15 to 40 wt. % of the formulation. The boosted bargain detergent preferably also includes water, typically an amount within the range of to 90 wt. %, more preferably from 50 to 80 wt. %, and most preferably from 60 to 70 wt. %.

The boosted bargain detergent can also take on many different forms, as described earlier. Thus, it can be a liquid, powder, paste, granule, tablet, molded solid, water-soluble sheet, or water-soluble sachet. Usually, the boosted bargain detergent is in the form of a liquid.

Both the performance booster for the bargain detergent and the surfactant composition used in the detergent for cold-water cleaning derive from a metathesis-derived $C_{10}$-$C_{17}$ monounsaturated acid, octadecene-1,18-dioic acid, or their ester derivatives. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived surfactants used in the inventive laundry detergents, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to surfactant compositions made from them, including, for example, modified physical form, melting range, compactability, and other important properties. These differences should allow formulators that use surfactants greater latitude or expanded choice as they use them in cleaners, fabric treatment, personal care, agricultural uses, and other end uses, particularly in laundry detergents.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized, the alkyl ester mixture will include a $C_{18}$ unsaturated diester.

When the natural oil is cross-metathesized with an α-olefin, the alkyl ester mixture includes a $C_{10}$ unsaturated alkyl ester and one or more $C_{11}$ to $C_{17}$ unsaturated alkyl ester coproducts. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making surfactants for the inventive laundry detergents.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty acid residues derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to anionic surfactant compositions for the inventive laundry detergents.

An alternative to using a natural oil as a feedstock to generate the $C_{10}$-$C_{17}$ monounsaturated acid, octadecene-1, 18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

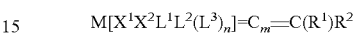

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

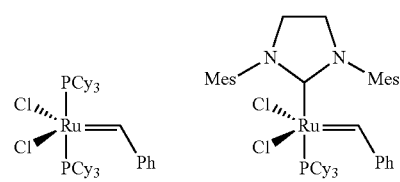

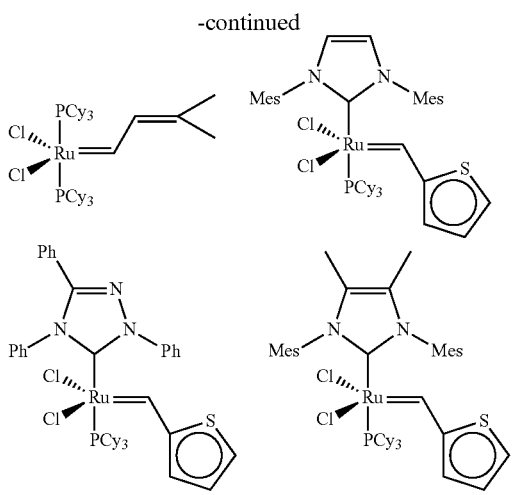

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The metathesis-derived $C_{10}$-$C_{17}$ monounsaturated acid, octadecene-1,18-dioic acid, or their ester derivatives are converted to particular subclasses of amides, betaines, amidoamines, amidoamine sulfonates, fatty ester alkoxylates, amidoamine oxides, amidoamine sulfobetaines, and other compositions that are useful either as surfactant compositions for cold-water laundry detergents or as performance boosters for bargain detergents. General synthetic procedures for making these compositions are provided below (General procedures C-K) and are summarized for each particular composition prepared in Table 2. For instance, betaine C10-41 is conveniently made using Methods E, C, and J by reacting methyl 9-decenoate with dimethylamine to make the N,N-dimethylamide, followed by reduction of the amide to an amine with lithium aluminum hydride, followed by quaternization of the amine to a betaine with sodium monochloroacetate. This composition is valuable for use in an MES-based detergent for cold-water cleaning. In another example, C12-33, a composition useful as a performance booster for a bargain detergent, is made using Methods F and J by reacting an unsaturated fatty acid with an alcohol ethoxylate to give an ethoxylated fatty acid methyl ester, followed by sulfitation of the olefin group.

Detergents for cold-water cleaning comprise—in addition to the anionic surfactant, nonionic surfactant, and fatty alkyl ester sulfonate—a surfactant composition derived from a metathesis-derived $C_{10}$-$C_{17}$ monounsaturated acid, octadecene-1,18-dioic acid, or their ester derivatives. This composition is selected from $C_{10}$ betaines, $C_{12}$ or $C_{16}$ amidoamines, $C_{12}$ ethanolamine amides, $C_{16}$ amidoamine sulfonates, $C_{18}$ diamidoamine dioxides, quaternized $C_{18}$ diamidoamine betaines, sulfonated $C_{18}$ low-EO fatty ester alkoxylates, $C_{18}$ amidoamine carboxylates, and amidoamine oxides and sulfobetaines derived from cross-metathesis of palm or soybean oil. Preferably, the composition is selected from $C_{10}$ betaines, $C_{12}$ amidoamines, $C_{12}$ ethanolamine amides, and $C_{16}$ amidoamine sulfonates.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

As used herein, "low-EO" alkoxylates have an average of 0.5 to 5 EO units, "mid-EO" alkoxylates have an average of 5 to 15 EO units, and "high-EO" alkoxylates have an average of 15 to 50 EO units.

In one preferred aspect of the invention, the metathesis-derived composition is a $C_{12}$ amidoamine made by reacting a $C_{12}$ monounsaturated acid or ester derivative with dimethylaminopropylamine (DMAPA). A particularly preferred composition of this type has the structure:

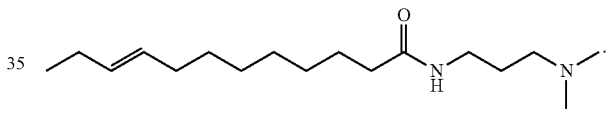

In another preferred aspect, the composition useful for cold-water cleaning is a $C_{10}$ betaine made by reacting a $C_{10}$ monounsaturated acid or ester derivative with dimethylamine, followed by reduction of the resulting amide, followed by quaternization to give the betaine. A particularly preferred composition of this type has the structure:

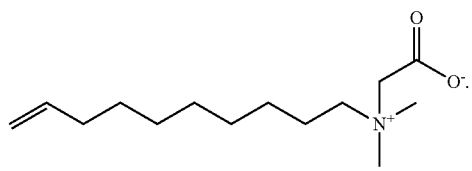

In another preferred aspect, the composition useful for cold-water cleaning is a $C_{12}$ ethanolamine-based amide made by reacting a $C_{12}$ monounsaturated acid or ester derivative with monoethanolamine. A particularly preferred composition of this type has the structure:

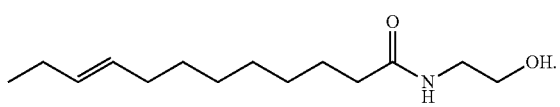 [SMILES: CC/C=C/CCCCCCCC(=O)NCCO]

In another preferred aspect, the composition useful for cold-water cleaning is a $C_{16}$ amidoamine sulfonate, which is conveniently made by sulfitation of the corresponding amidoamine. A preferred composition of this type has the structure:

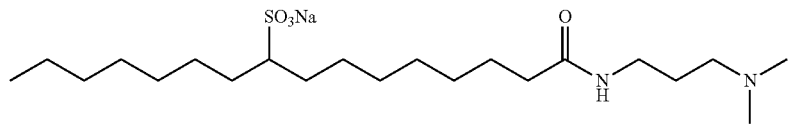

In another preferred aspect, the composition useful for cold-water cleaning is a $C_{18}$ diamidoamine dioxide made by reacting an octadecene-1,18-dioic acid or its ester derivative with dimethylaminopropylamine, followed by oxidation of the resulting diamine. A particularly preferred composition of this type has the structure:

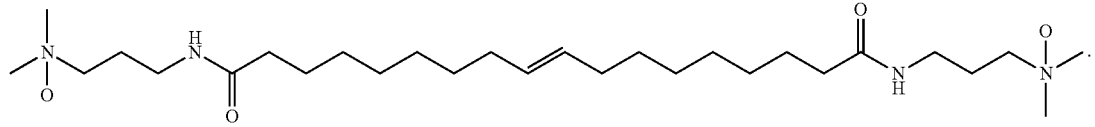

In another preferred aspect, the composition useful for cold-water cleaning is an amidoamine oxide or sulfobetaine derived from cross-metathesis of palm or soybean oil. Illustrative compositions of this type include the sulfobetaine product made by cross-metathesis of soybean oil with 1-butene:

Boosted bargain detergents of the invention comprise—in addition to the anionic surfactant, and nonionic surfactant—a performance booster derived from a metathesis-derived $C_{10}$-$C_{17}$ monounsaturated acid, octadecene-1,18-dioic acid, or their ester derivatives. The booster is selected from $C_{12}$ low-EO fatty ester alkoxylate sulfonates, $C_{18}$ amidoamine oxide esters, $C_{18}$ amidoamine oxide carboxylates, and amidoamine sulfobetaines made from self-metathesized palm or soybean oil.

In one preferred aspect, the booster is a $C_{12}$ low-EO fatty ester ethoxylate sulfonate made, for example, by reacting a $C_{12}$ monounsaturated acid or ester derivative with an ethylene glycol alkyl ether, followed by sulfitation of the olefin. A particularly preferred booster of this type has the structure:

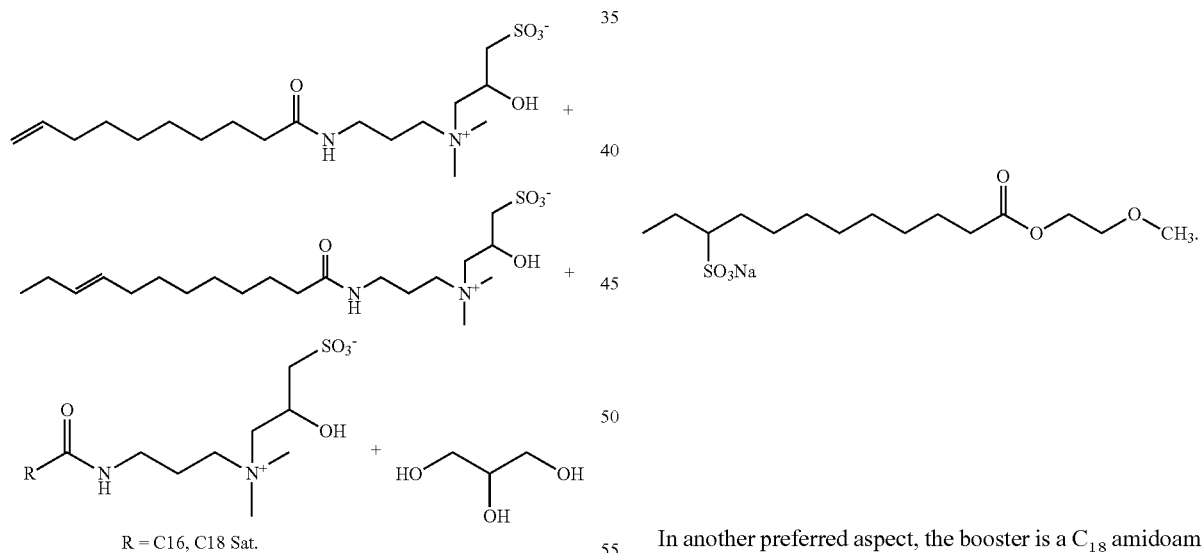

In another preferred aspect, the booster is a $C_{18}$ amidoamine oxide ester. A particularly preferred booster of this type has the structure:

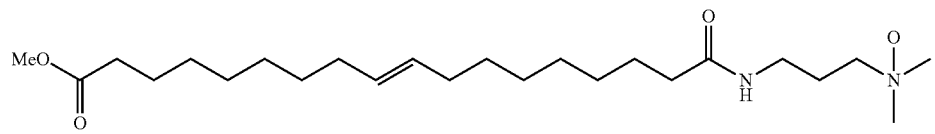

In another preferred aspect, the booster is an amidoamine sulfobetaine made from self-metathesized palm or soybean oil. The sulfobetaine product from self-metathesis of palm oil is illustrative:

kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the

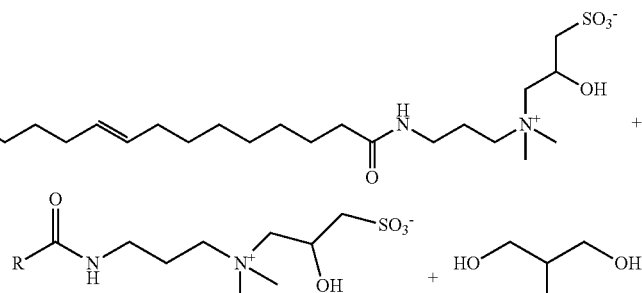

The laundry detergent formulations can include additional conventional components. For instance, the formulation can include one or more additives such as alkalinity agents, builders, buffers, abrasives, electrolytes, bleaching agents, brighteners, fragrances, dyes, foaming control agents, antistatic agents, wrinkle-reduction agents, soil-release agents, chelating agents, suds suppressors, soil repellants, anti-redeposition agents, antimicrobial agents, thickeners, pigments, gloss enhancers, enzymes, detergents, surfactants, cosolvents, dispersants, hydrotropes, speckles, and the like. For examples of additional conventional components, see U.S. Pat. Nos. 7,078,373 and 7,820,612, and U.S. Pat. Appl. Publ. Nos. 2008/0009430 and 2010/0016198, the teachings of which are incorporated herein by reference.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

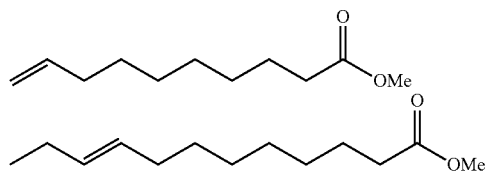

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt %), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 μtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 ptorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (μtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Preparation of Methyl 9-Hexadecenoate ("C16-0") Feedstock

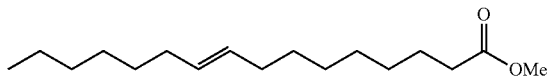 [SMILES: CCCCCC/C=C/CCCCCCCC(=O)OC]

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

Quaternization: General Procedure C

Tertiary amines are converted to methyl quats, betaines, or sulfobetaines by reaction with a quaternizing agent. The quaternization is performed at temperature within the range of 65° C. to 100° C. The quaternizing agent used is dimethyl sulfate for methyl quats, sodium monochloroacetate for betaines, or epichlorohydrin for sulfobetaines. The amount of quaternizing agent used is from 0.8 to 1.0 molar equivalents based on the amount of tertiary amine. The reaction is deemed complete when the free amine value is in the desired range as determined by perchloric acid titration.

Amine Oxides from Amines: General Procedure D

A tertiary amine is diluted with water to form a 10-40 wt. % mixture, which is warmed to 50° C. to 75° C. under nitrogen. Hydrogen peroxide solution (35% solution, 1 to 2.2 molar eq.) is added dropwise while keeping the temperature below 75° C. The mixture is held at the reaction temperature for 4 to 12 h or until the free peroxide level is below 0.2% as determined by starch iodide paper.

Amide Synthesis (Including Amidoamines): General Procedure E

Unsaturated methyl ester (C10, $C_{12}$, or $C_{16}$ monoester or $C_{18}$ diester) is combined with 1-6 molar equivalents of a primary or secondary amine (e.g., DMA, DEA, MEA, DMAPA). A base catalyst (e.g., NaOMe or other alkoxide) is added if desired. The reaction mixture is heated at a temperature within the range of 50° C. to 150° C. until the starting ester is substantially consumed. The amide product is purified by distillation, water washing, or other normal means. Alternatively, the product is used "as is" and converted to other derivatives.

Esterification to Make Ethoxylates (eFAMEs): General Procedure F

A suitable carboxylic acid is combined with a poly(ethylene glycol)monomethyl ether (0.8-2.5 eq.), an acid catalyst (e.g., sulfuric acid, methanesulfonic acid, p-toluenesulfonic acid, or the like), and optionally a solvent (e.g., toluene, xylene, or other hydrocarbons capable of forming a water azeotrope). The mixture is heated at 120° C. to 180° C. under vacuum, nitrogen sparge, or nitrogen blanket and the liberated water is collected. The reaction continues until the desired acid value is achieved.

Amines by Amide Reduction: General Procedure G

Lithium aluminum hydride (or a similar reducing agent) is dissolved in a solvent (e.g., diethyl ether, THF, dioxane, diglyme) under a nitrogen blanket. A suitable fatty amide is dissolved in the same solvent and is added dropwise, keeping the reaction temperature within the range of 25° C. to 50° C. After the addition, the mixture is stirred overnight at room temperature. Water is carefully added to quench the reaction, and aqueous sodium hydroxide is added. The solids are filtered off, and the solvent is removed. The amine product is purified by distillation.

Imidazoline Synthesis: General Procedure H

Methyl 9-decenoate or methyl 9-dodecenoate is combined with diethylenetriamine (DETA), with or without a catalyst, in the desired molar ratio of ester groups to primary amino and/or hydroxyl groups. Usually, two moles of ester are used for each mole of DETA. The mixture is heated with agitation to a temperature within the range of 140° C. and 200° C. under a mild vacuum that prevents or minimizes evaporation of DETA from the reaction mixture. The reaction proceeds until analysis (IR or $^1$H NMR spectroscopy) indicates reasonably complete conversion. The contents are then heated at a temperature within the range of 175° C. to 300° C. with a lower vacuum (5-100 mm Hg) to effect ring closure to the imidazoline. Reaction end point is determined by titration.

Sulfitation of Olefins: General Procedure J

A sulfitating agent (sodium sulfite, sodium bisulfite, sodium metabisulfite, or the like) is dissolved in water and combined with at least a molar equivalent of an olefin. Optionally, a catalyst (peroxides, iron, or other free-radical initiators) is included. The mixture is heated to 50° C.-100° C. for 3-15 h until sulfitation is reasonably complete.

Estolide Preparation: General Procedure K

The procedure used to convert methyl ester C10-0 to its respective fatty acid C10-36 is generally followed as described below.

Sulfonation is carried out in a batch reactor maintained at 20° C. under a nitrogen flow (2 L/min.). The unsaturated fatty acid or an unsaturated fatty acid and saturated fatty acid mixture is added to methylene chloride. Sulfur trioxide is evaporated over 30 min. via a 140° C. flash-pot and is bubbled through the reactor using the nitrogen stream at a molar ratio of $SO_3$ to alkene functionality of about 1:1. The addition rate of $SO_3$ is adjusted to keep the reaction temperature at or below 35° C. At the end of the addition, the reaction mixture is maintained for an additional 5 min. and the mixture is then concentrated under vacuum. The acid product is digested for 1-2 h at 50-85° C. Neutralization is performed using an appropriate base and hydrolysis occurs at 85° C. with the pH maintained with additional base. $^1$H NMR is used to determine complete hydrolysis.

Ester Hydrolysis to Fatty Acid: General Procedure L

The procedure used to make fatty acid C10-36 as outlined in detail below is generally used.

Table 2 summarizes the general procedures used to prepare the following compositions:

TABLE 2

General Methods Used to Synthesize Compositions

| Composition | Methods |
| --- | --- |
| C10-17 | E |
| C10-18 | E, C |
| C10-19 | E, C, J |
| C10-20 | E, D |
| C10-21 | E, D, J |
| C10-22 | E, C |
| C10-25 | E |
| C10-32* | K |
| C10-40 | E, G, C |
| C10-41* | E, G, C |
| C12-14 | H, C, J |
| C12-17* | E |
| C12-19 | E, C, J |
| C12-20 | E, D |
| C12-24 | E, C |
| C12-30* | E |
| C12-33* | F, J |
| C12-34 | K |
| C12-38 | E |
| C16-9 | E |
| C16-11 | E, J |
| Mix-26 | E |
| C18-28 | E, C, J |
| C18-29* | E, D |
| C18-30 | E, D, J |
| C18-32 | E, C |
| C18-33 | E, C, J |
| C18-34 | E, C |
| C18-36 | E, C |
| Mix-36 | E, C |
| C18-37 | E, C, D |
| Mix-37 | E, C, D |
| C18-38 | E, C |
| Mix-38* | E, C |
| Mix-46 | E, D |
| Mix-61 | F, J |
| C18-68 | E, J |
| Mix-70 | E, L |
| Mix-73 | E, L, D |
| MTG-6 | E, C |
| PMTG-11 | E, C |

TABLE 2-continued

General Methods Used to Synthesize Compositions

| Composition | Methods |
|---|---|
| UTG-11 | E, C |
| UTG-12 | E, D |

Methods: C: quaternization to methyl quat, betaine, or sulfobetaine; D: oxidation of amine to amine oxide; E: amide from unsaturated ester and primary or secondary amine; F: ethoxylated fatty acid methyl ester from unsaturated fatty acid; G: amine from amide by reduction; H: imidazoline synthesis from unsaturated methyl esters; J: sulfitation of olefins; K: estolide preparation; L: ester hydrolysis to carboxylate

*A detailed synthetic procedure for this composition is included hereinbelow.

Each of the following compositions is tested either as a surfactant component of an MES-based cold-water cleaning detergent or as a booster for a bargain laundry detergent. Unless otherwise indicated below, the compositions are prepared using the general methods summarized in Table 2:

C10-17: C10 DMAPA Amide

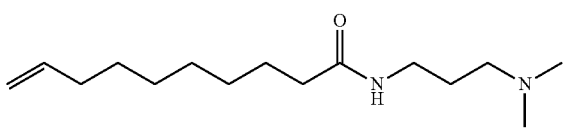

C10-18: C10 DMAPA Quat

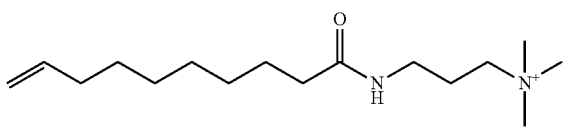

C10-19: C10 DMAPA Quat Sulfonate

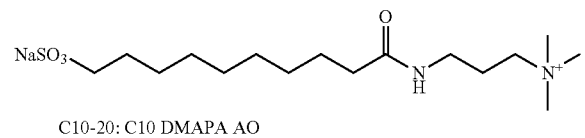

C10-20: C10 DMAPA AO

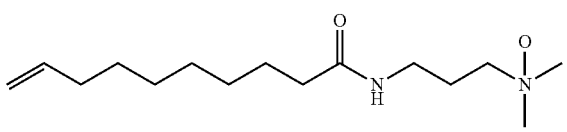

C10-21: C10 DMAPA AO Sulfonate

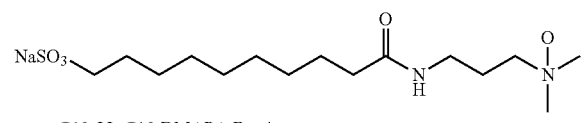

C10-22: C10 DMAPA Betaine

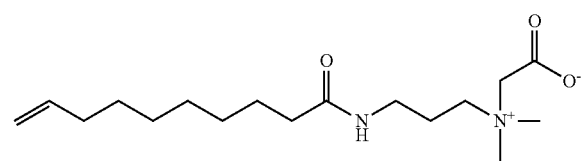

C10-25: C10 DMA Amide

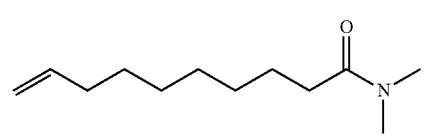

C10-36: C10 Fatty Acid

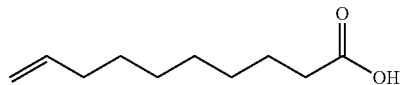

Methyl ester C10-0 (390.2 g) is charged to a round-bottom flask equipped with an overhead stirrer, and the contents are warmed to 70° C. Potassium hydroxide (16% solution in glycerin, 523 g) is added. The mixture is heated to 100° C. and additional KOH pellets (35.10 g) are added. After stirring 17 h, gas chromatography indicates ~94% conversion to the fatty acid. Additional KOH (10 g) is added, and stirring continues at 100° C. for 4 h. Conversion by GC is >97%. The mixture stirs at 100° C. for another 4 h, and is then cooled to 80° C. Water (400 mL) and 30% sulfuric acid solution (500 mL) are added, and the mixture stirs for 1 h. The aqueous phase is then removed. Water (500 mL) is added, and heating/stirring resumes (to 80° C.) for 0.5 h. The aqueous phase is again removed. The water washing process is repeated two more times (2×500 mL). The crude fatty acid product is stripped under vacuum at 80° C. for 2 h to remove water and is used without further purification. Yield: 357 g.

C10-32: C10 UFA SLA

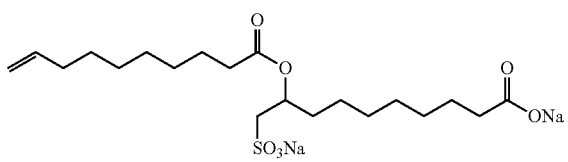

In a sulfonation batch reactor maintained at 20° C. under a nitrogen flow (2 L/min.), C10-36 (109.6 g, 0.64 mol) is added to methylene chloride (100 mL). Sulfur trioxide (51.6 g, 0.64 mol) is evaporated over 30 min. via a 140° C. flash-pot and is bubbled through the reactor using the nitrogen stream. The addition rate of $SO_3$ is adjusted to keep the reaction temperature at or below 35° C. At the end of the addition, the reaction mixture is maintained for an additional 5 min. and the mixture is then concentrated under vacuum. The acid product is then digested for 1 h at 50° C. The acid is neutralized using water (151.0 g) followed by 50% aq. NaOH (41.7 g). Hydrolysis is carried out at 85° C. and pH is maintained with additional 50% aq. NaOH additions. $^1$H NMR analysis supports the proposed composition for sulfo-estolide C10-32. Analytical results: pH: 5.25 (as is); moisture: 51.6 wt. %; sodium sulfate: 0.51 wt. %;

C10-40: C10 Benzyl Quat

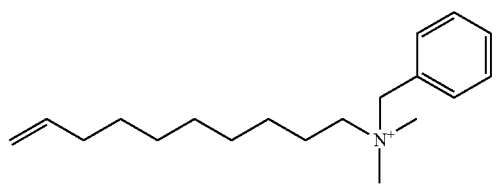

C10-41: C10 Betaine

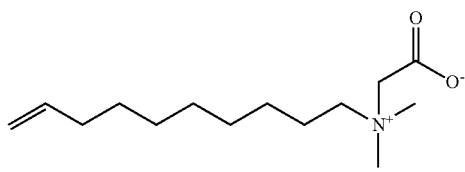

A round-bottom flask is charged with methyl ester C10-0 (235 g) and the feedstock is degassed with nitrogen. Sodium methoxide (5 g of 30% solution in methanol) is added via syringe over 5 min. and full vacuum is applied. Dimethylamine (67 g) is slowly added via sub-surface dip tube. After the addition, the mixture is heated to 60° C. and held overnight. The amide, C10-25, is recovered via vacuum distillation (120° C., 20 mm Hg). Iodine value: 128.9 g $I_2$/100 g sample. $^1$H NMR (CDCl$_3$), δ (ppm): 5.8 (CH$_2$=CH—); 4.9 (CH$_2$=CH—); 2.8-3.0 (—C(O)—N(CH$_3$)$_2$; 2.25 (—CH$_2$—C(O)—).

Amide C10-25 (475 g) is slowly added over 3 h to a stirring THF slurry of LiAlH$_4$ (59.4 g) under nitrogen while maintaining the temperature at 11-15° C. The mixture warms to room temperature and stirs overnight. The mixture is chilled in an ice bath, and water (60 g) is added cautiously, followed by 15% aq. NaOH solution (60 g). The mixture warms to room temperature and is stirred for 1 h. The mixture is filtered, and the filter cake is washed with THF. The filtrates are combined and concentrated. Phthalic anhydride (57.5 g) is added in portions, and the mixture is vacuum distilled to isolate C10-38. Amine value: 298.0 mg KOH/g; iodine value: 143.15 g $I_2$/100 g sample; % moisture: 0.02%. $^1$H NMR (CDCl$_3$), δ (ppm): 5.8 (CH$_2$=CH—); 4.9 (CH$_2$=CH—); 3.7 (—CH$_2$—N(CH$_3$)$_2$).

A flask is charged with C10-38 (114 g), water (180 mL), and sodium monochloroacetate (74.6 g). The mixture is heated to 100° C. and the pH is maintained at 7-9 by adding 50% NaOH. After 6 h, titration shows 9.7% chloride (theoretical: 10%). Upon cooling, C10-41 is analyzed: moisture: 49.58%; NaCl=9.95%. $^1$H NMR (D$_2$O), δ: 5.8 (CH$_2$=CH—); 4.9 (CH$_2$=CH—); 3.7 (—CH$_2$—N$^+$(CH$_3$)$_2$); 3.1 (—CH$_2$—N$^+$(CH$_3$)$_2$).

C12-14: C12 DETA Quat Sulfonate

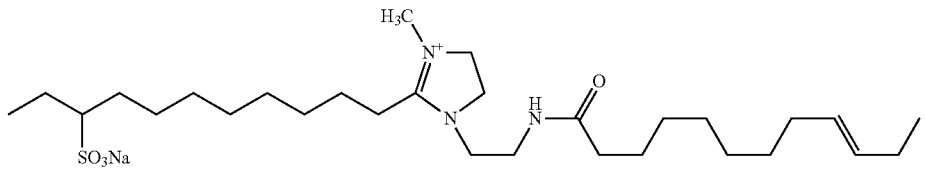

C12-17: C12 DMAPA Amide

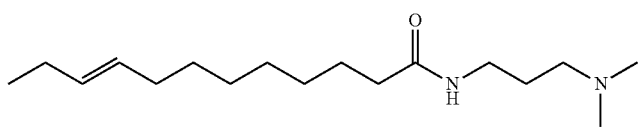

A round-bottom flask equipped with nitrogen sparge tube, mechanical stirrer, and Dean-Stark trap is charged with methyl ester C12-0 (670 g), 3-(dimethyl-amino)propylamine ("DMAPA," 387 g), and sodium methoxide (11.2 g of a 30% solution of in methanol). The reaction mixture is heated to 100° C. and methanol is collected. The reaction temperature is increased in 5° C. increments until the temperature reaches 130° C. The mixture is held at 130° C. for 1 h, and then a sub-surface nitrogen sparge is applied for 2.5 h. The temperature is elevated to 140° C. for an additional 3.5 h. Collected distillate includes methanol and some DMAPA. The reaction mixture is cooled to 110° C., the nitrogen sparge is discontinued, and vacuum was applied. The mixture is stripped of excess DMAPA (150° C., 20 mm Hg, 30 min.). The product, amidoamine C12-17, has an amine value of 196.39 (eq. wt.: 281.3). $^1$H NMR (CDCl$_3$) confirms formation of the amide, based on disappearance of the methyl ester peak at 3.61 ppm and appearance of the DMAPA CH$_2$ signals at 3.30, 2.11, and 1.62 ppm and the N(CH$_3$)$_2$ at 2.20 ppm.

C12-19: C12 DMAPA Quat Sulfonate

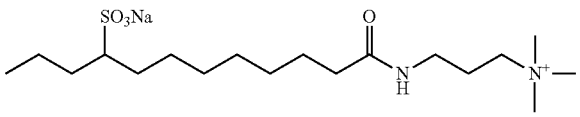

C12-20: C12 DMAPA AO

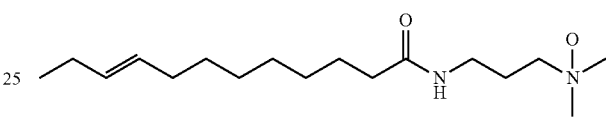

C12-24: C12 DMAPA Sulfobetaine

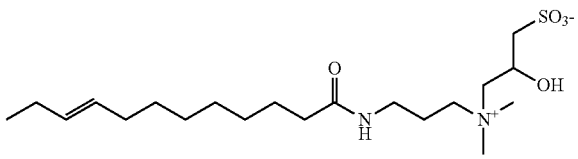

C12-30: C12 MEA Amide

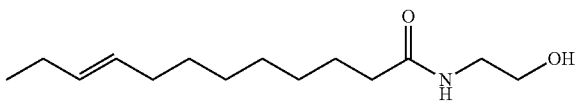

A round-bottom flask equipped with nitrogen sparge, thermocouple, heating mantle, agitator, and Dean-Stark trap is charged with methyl ester feedstock C12-0 (125.1 g, 0.596 mol) and monoethanolamine (37.2 g, 0.608 mol). The mixture is heated to 60° C. Sodium methoxide (2.14 mL of 30 wt. % solution in methanol, 0.012 mol) is added to the flask, and the reaction exotherms to ~80° C. The mixture is then heated to 100° C. and held for 2.5 h. The reactor is cooled to 90° C. and the Dean-Stark trap is removed. Vacuum is applied incrementally to 20 mm Hg over 0.5 h. Vacuum was held at 20 mm Hg for 0.5 h, then at 1.4 mm Hg for 1.0 h to remove residual methanol. $^1$H NMR spectroscopy indicates reasonably complete conversion to C12-30. Free MEA, determined by titration, is 0.71%.

C12-33: C12 eFAME Sulfonate

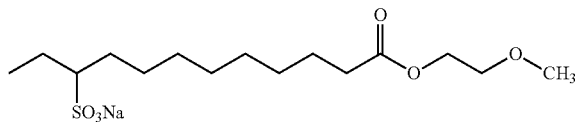

C12-39 fatty acid (208.0 g, 1.022 mol) is charged to a round-bottom flask equipped with an overhead stirrer, Dean-Stark trap, reflux condenser, thermocouple, heating mantle, and temperature controller. 2-Methoxyethanol (162.0 g) and toluene (500 mL) are added. The mixture is heated to 124° C. while p-toluenesulfonic acid (1.7 g) is added. Water of reaction begins to collect when the target temperature is reached. Heating continues for 3 h, and conversion to the eFAME (by $^1$H NMR) is 98%. (Signals for the hydrogens alpha to the carbonyl are used to determine degree of conversion.) The sample is stripped to remove toluene and excess 2-methoxyethanol. Residual toluene is removed by stirring at 150° C. under vacuum (1-5 mm Hg) with a low nitrogen sparge to give ethoxylated fatty acid methyl ester C12-8.

A round-bottom flask equipped with stir bar, thermocouple, heating mantle, temperature controller, and pH probe is charged with C12-8 (109.7 g) and isopropyl alcohol (110.0 g). The initial pH is 6. The contents are heated to 45° C., and t-butylperoxybenzoate (2.0 mL) is added. Separately, sodium bisulfite (as $Na_2S_2O_5$, 41.5 g) and sodium sulfite (8.0 g) are dissolved in deionized water (137.5 g). This solution is added dropwise to the olefin mixture. A precipitate forms initially, but later dissolves. The pH is adjusted to 7 by adding sodium hydroxide and the mixture stirs overnight at 25° C. $^1$H NMR indicates no reaction after three nights. The mixture is transferred to another vessel with deionized water (362.5 g, sodium sulfite (2.7 g), and TBB (2.0 mL), and the mixture is heated to 75° C. for 3 h, then cooled to room temperature and stirred for 2 days. $^1$H NMR shows 80% conversion. The mixture is reheated to 75° C. for 5 h, then cooled to room temperature and stirred overnight. No additional conversion occurs. Isopropyl alcohol is stripped and chloroform is added to isolate unreacted C12-8 (aqueous phase) from the sulfonated product, C12-33 (chloroform phase).

C12-34: C12 UFA SLA

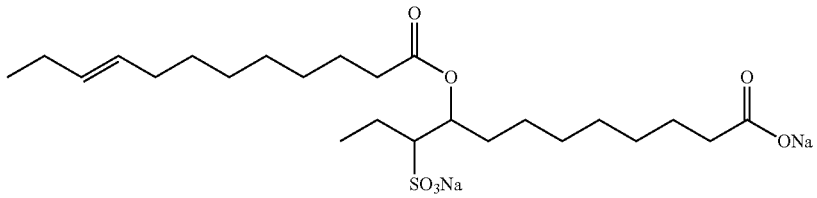

C12-38: C12 MIPA Amide

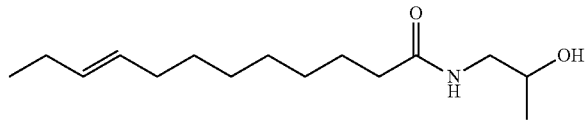

C16-9: C16 DMAPA Amide

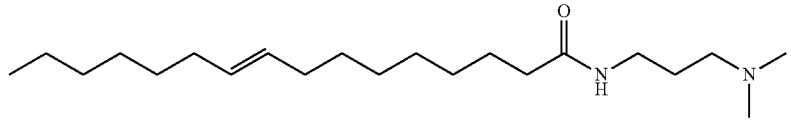

C16-11: C16 DMAPA Sulfonate

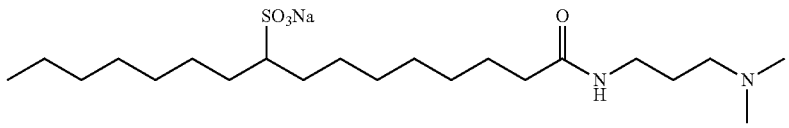

Feedstock Synthesis

Preparation of Dimethyl 9-Octadecene-1,18-dioate ("Mix-0" or "C18-0")

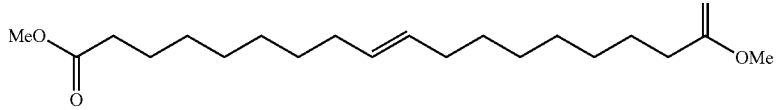

Eight samples of methyl 9-dodecenoate (10.6 g each, see Table 3) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenyl idene)-(tricyclohexylphosphine), product of Materia) is added to the methyl 9-dodecenoate (amount indicated in Table 3) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 3. "Mix-0" is an 80:20 trans-/cis-isomer mixture obtained from the reaction mixture. Crystallization provides the all-trans-isomer feed, "C18-0."

TABLE 3

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methy 9-dodecenoate

The tested compounds based on $C_{18}$ feedstock have the following structures:

A round-bottom flask equipped with a mechanical stirrer is charged with diester C18-0 (545.6 g) and DMAPA (343.3 g). A Dean-Stark trap is attached, and sodium methoxide (20 g of 30 wt % solution in MeOH) is added. The temperature is raised to 110° C. over 1.5 h, and methanol is collected. The temperature is increased to 150° C. in increments as the distillation slows. The mixture is held at 150° C. for 6.5 hours and then cooled to room temperature. $^1$H NMR analysis indicates a minor amount of unreacted methyl ester. The mixture is heated to 180° C. for several hours and additional DMAPA and sodium methoxide are added. The mixture is cooled and neutralized with concentrated hydrochloric acid. When the mixture has cooled to 90° C., deionized water is added, resulting in precipitation of the amide to afford a slurry. Solids are isolated by vacuum filtration and washed with water. The solid product, all-trans amide C18-26, is dried under vacuum. Yield: 92.2%. $^1$H NMR (CDCl$_3$) confirms formation of the amide, based on disappearance of the methyl ester peak at 3.65 ppm and appearance of the DMAPA CH$_2$ signals at 3.31, 2.12, and 1.62 ppm and the N(CH$_3$)$_2$ at 2.20 ppm.

A round-bottom flask is charged with amine C18-26 (141.0 g), water (231.2 g), and Hamp-Ex 80 (0.4 g). The mixture is heated to 50° C. and dry ice is added to pH 8.8. When the pH stabilizes, aqueous H$_2$O$_2$ (35%, 57.8 g) is added dropwise without heating, keeping the temperature below 75° C. After the peroxide addition is complete, the mixture is warmed at 85° C. for 18 h. The mixture is cooled to room temperature to give di-AO C18-29. Titrations reveal: amine oxide: 1.32 meq/g; free amine: 0.027 meq/g; free peroxide: 0.0019%; water: 66.4%.

Mix-26: C18 DiDMAPA Amide (80:20 trans-/cis-)

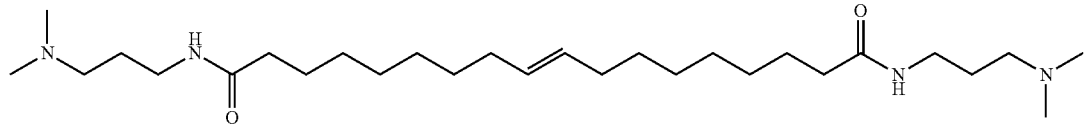

C18-28: C18 DiMIPA DiQuat Sulfonate

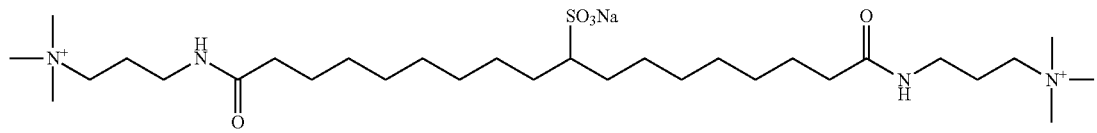

C18-29: C18 DiDMAPA DiAO (100% trans-)

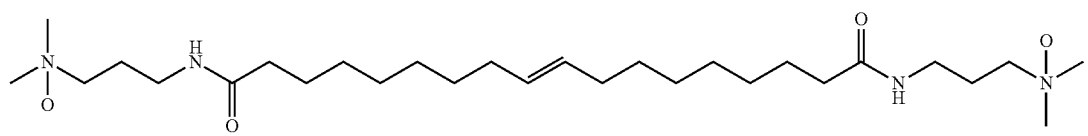

C18-30: C18 DiDMAPA DiAO Sulfonate

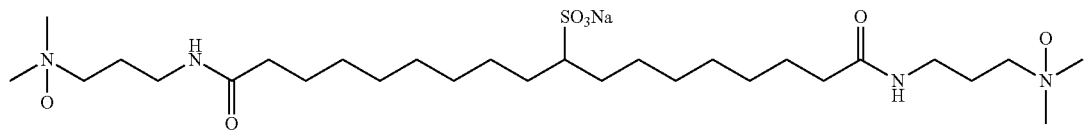

C18-32: C18 DiBetaine (100% trans-)

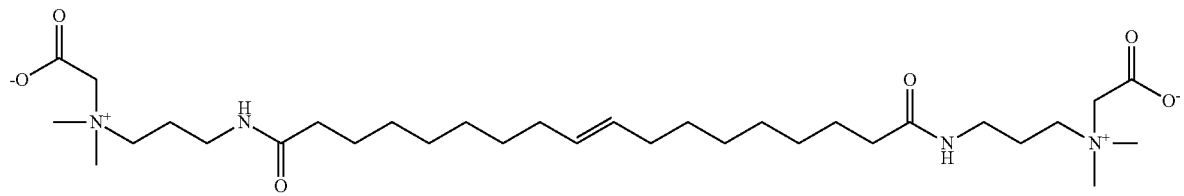

C18-33: C18 DiBetaine Sulfonate

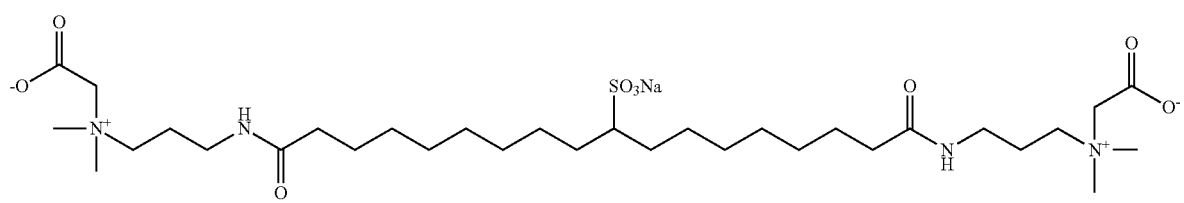

C18-34: C18 DiDMAPA MonoQuat (100% trans-)

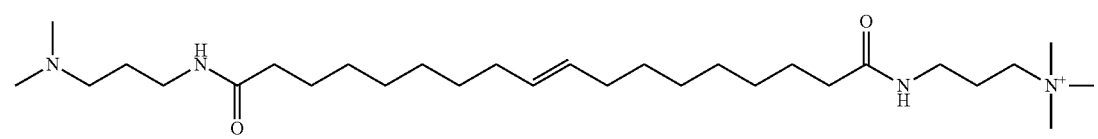

C18-36: C18 DiDMAPA Monobetaine (100% trans-)
MIX-36: C18 DiDMAPA Monobetaine (80:20 trans-/cis-)

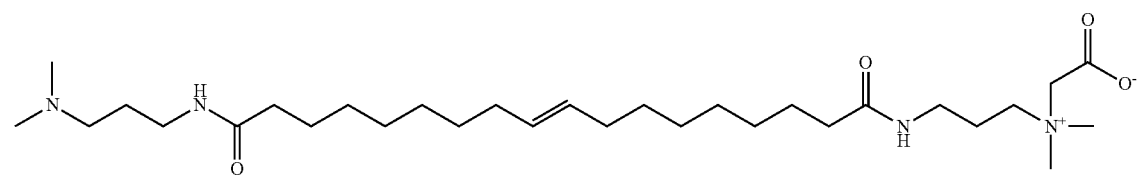

C18-37: C18 DiDMAPA Betaine AO (100% trans-)
MIX-37: C18 DiDMAPA Betaine AO (80:20 trans-/cis-)

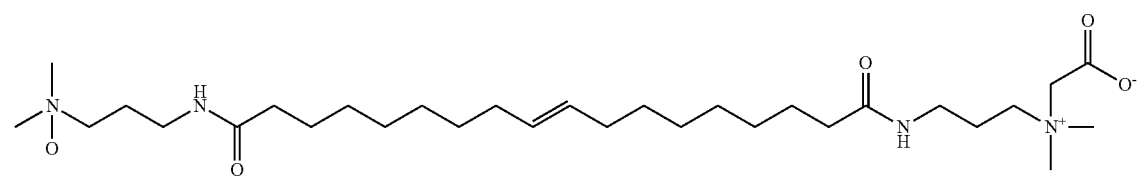

C18-38: C18 DiDMAPA Betaine Quat (100% trans-)
MIX-38: C18 DiDMAPA Betaine Quat (80:20 trans-/cis-)

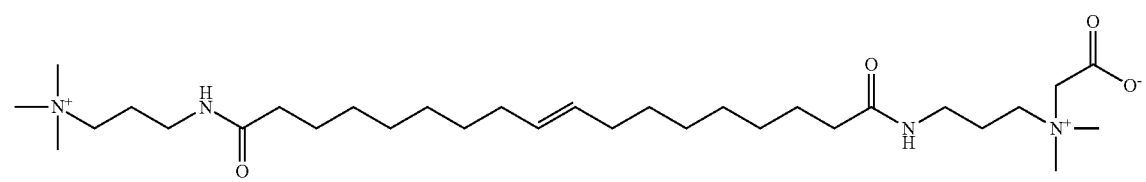

Dimethyl ester C18-0 (824.3 g), DMAPA (519.5 g), and sodium methoxide solution (2.4 wt. % NaOMe based on methyl ester) are heated slowly to 140° C. and held for several hours. A subsurface nitrogen sparge is utilized at the end to facilitate the removal of methanol. The temperature is reduced to 100° C., and the contents are vacuum stripped. A solution made from deionized water (1.0 L) and 50% $H_2SO_4$ (11 g) is added slowly to the molten reaction product. The mixture cools, and the pasty solids are isolated by filtration. The solids are washed with deionized water, and the filtrate is extracted with chloroform (2×250 mL). The chloroform extracts are concentrated, and the resulting yellow oil is identified as the cis-enriched product by $^1$H NMR. The yellow oil is redissolved in $CHCl_3$, filtered through silica, and combined with the pasty solids. Additional CHCl₃ (100 mL) is added to the contents, and the mixture is swirled on a rotary evaporator at 70° C. until homogeneous. Vacuum is applied, and the CHCl₃ is removed, followed by water. Evaporation is discontinues when the product remains a solid at 98° C. The cooled product, Mix-26, is analyzed: amine value: 229.1 mg KOH/g sample; free DMAPA: 0.08%; moisture: 0.09%; total alkalinity: 4.08 meq/g. $^1$H NMR (CDCl₃), δ (ppm)=5.3 (—CH=CH—); 3.25 (—C(O)—NH—CH₂—); 2.2 (—N(CH₃)₂). $^{13}$C NMR (CDCl₃), δ (ppm)=130 (trans-CH=CH—); 129.5 (cis, —CH=CH—). Product ratio: 79.3% trans, 20.7% cis.

Diamide Mix-26 (224.5 g) is charged to a flask with water (322 g) and citric acid (1.5 g), and the contents are heated to 80° C. Sodium monochloroacetate (57 g) in water (200 mL) is added slowly to avoid an exotherm. When the addition is complete, the mixture is heated to 90° C. and held for 6.5 h. Additional sodium monochloroacetate (3.5 g) is added, and the reaction continues at 90° C. for 2 h. Titration shows 3.82% free NaCl. The mixture is cooled, and the product is transferred to a round-bottom flask with methanol. The monobetaine product, Mix-36, is dried to a solid by repeatedly adding MeOH and evaporating on a rotary evaporator. $^1$H NMR (d₃-MeOD), δ (ppm)=5.35 (—CH=CH—); 3.8 (—C(O)—CH₂—N⁺(CH₃)₂—); 3.2 (—C(O)—CH₂—N⁺(CH₃)₂—).

A nitrogen-purged flask is charged with monobetaine Mix-36 (113.9 g), isopropyl alcohol (66 g), and ethanol (30 g). The mixture is warmed to 70° C. and dimethyl sulfate (15.65 g) is added dropwise. The mixture is cooled to maintain the temperature ~70° C. The mixture is held at 70° C. for 3 h. Additional dimethyl sulfate (0.96 g) is added, and heating continues at 70° C. for 3 h, then at 85° C. for 2 h. The mixture is allowed to cool and is concentrated. Water (195 g) is added to ~40 wt. % solids. Analysis of the betaine quat product, Mix-38, shows: pH: 8.35 (1% in water); moisture: 47.7 wt. %; NaCl: 4.74 wt. %; sodium sulfate: 0.3 wt. %. $^1$H NMR data support the proposed structure.

MIX-46: C18 Ester DMAPA AO (80:20 trans-/cis-)

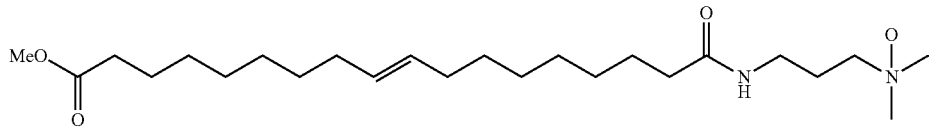

MIX-61: C18 eFAME Sulfonate (80:20 trans-/cis-)

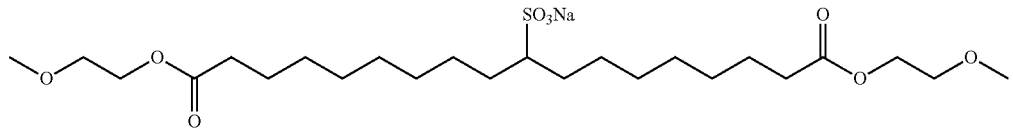

C18-68: C18 DiDMAPA Amide Sulfonate (100% trans-)

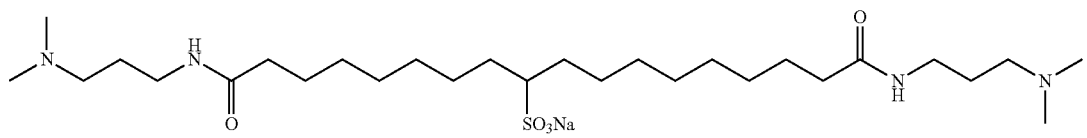

MIX-70: C18 DMAPA Carboxylate (80:20 trans-/cis-)

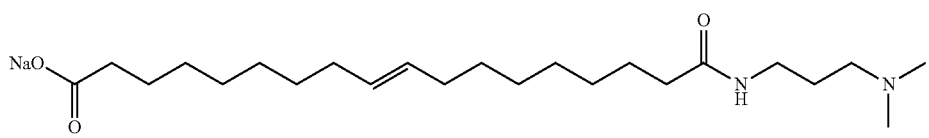

MIX-73: C18 Carboxylate DMAPA AO (80:20 trans-/cis-)

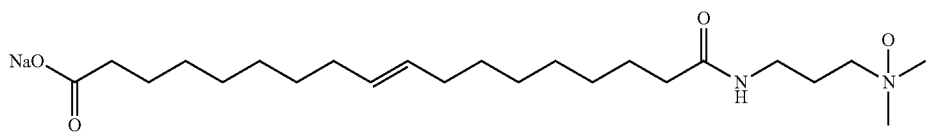

Modified Triglyceride Based on Soybean Oil ("MTG-0")

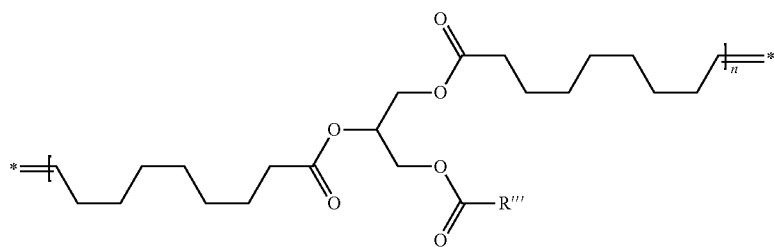

The procedures of Examples 1A and 1E are generally followed except that 1-butene is omitted.

Mod. Triglyceride From Cross-Metathesis of Soybean Oil and 1-Butene ("UTG-0")

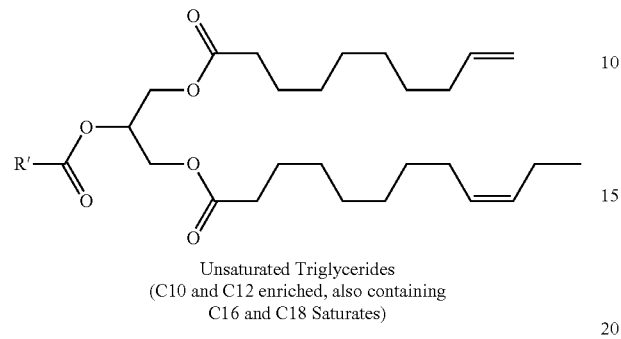

Unsaturated Triglycerides
(C10 and C12 enriched, also containing
C16 and C18 Saturates)

The procedures of Examples 1A and 1E are generally followed to produce UTG-0 from soybean oil and 1-butene.

Modified Triglyceride Based on Palm Oil ("PMTG-0")

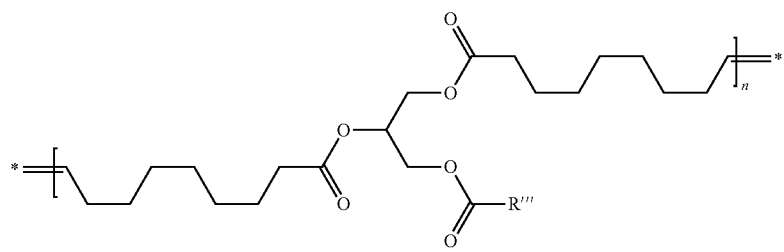

The procedure used to make MTG-0 is followed, except that palm oil is used instead of soybean oil.

MTG-0 Feedstock Derivatives

MTG-6: MTG DMAPA Betaine Mix

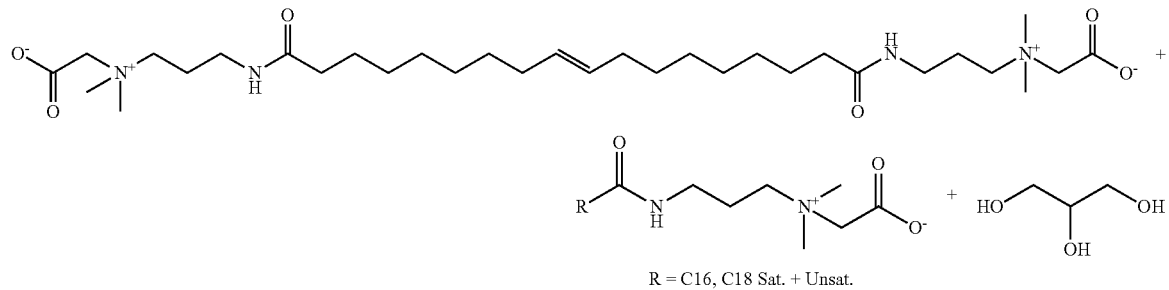

R = C16, C18 Sat. + Unsat.

PMTG-11: PMTG DMAPA Sulfobetaine

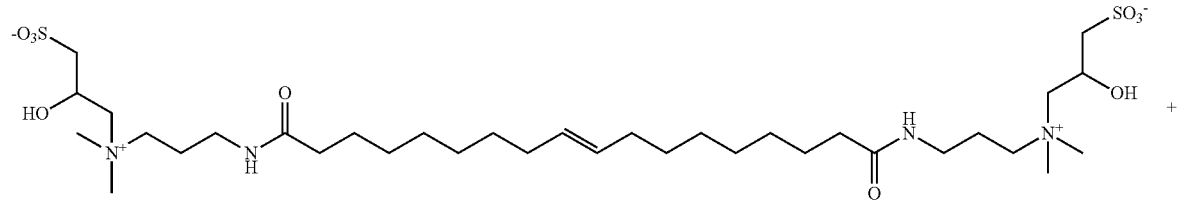

-continued

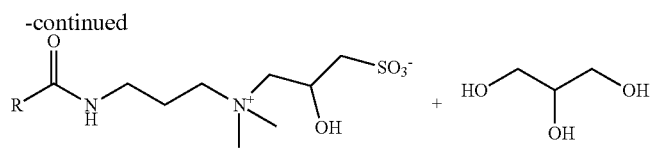

R = C16, C18 Sat. + Unsat.

UTG-11: UTG DMAPA Sulfobetaine

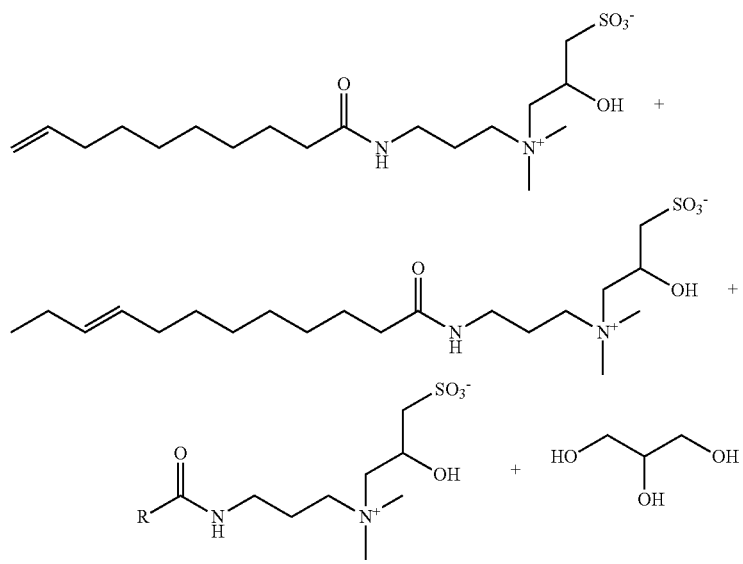

R = C16, C18 Sat.

UTG-12: UTG DMAPA AO

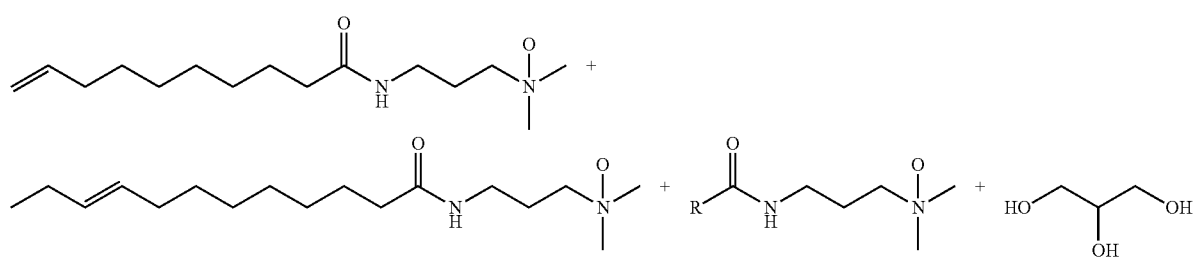

R = C16, C18 Sat.

TABLE 4

Summary of Modified Triglyceride Products

| | Soybean Oil | | Palm Oil | |
|---|---|---|---|---|
| | Self-met. MTG-0 | X-met. UTG-0 | Self-met. PMTG-0 | X-met. PUTG-0 |
| DMAPA Betaine Mix | MTG-6 | — | — | — |
| DMAPA Sulfobetaine | — | UTG-11 | PMTG-11 | — |
| DMAPA AO | — | UTG-12 | — | — |

Part A. Solubility Evaluation of $C_{16}$ MES Concentrates

This method evaluates the ability of an experimental sample to prevent precipitation of a $C_{16}$-based methyl ester sulfonate ("$C_{16}$ MES") in an ultra laundry detergent formula at 5° C. and 25° C. storage temperatures. Although $C_{16}$ MES provides good cleaning over a broad range of soils, it is difficult to incorporate it into laundry detergents because of its relatively poor solubility in water and common surfactants.

A concentrated blend containing most of the detergent components is first prepared. The blend is then combined with $C_{16}$ MES, water, and the experimental sample to be tested. Performance of the experimental sample is compared with that of Ninol® 40-CO, a commercial cocamide DEA (product of Stepan Company).

Preparation of Concentrated Blend:

Deionized water (90% of the required total amount) is first combined and mixed at 50° C. with Bio-Soft® S-101 (dodecylbenzene sulfonic acid, 3.27 wt. %, product of Stepan). Sodium hydroxide (50% aq. solution) is added to pH 11 (about 24% of the total amount of 4 wt. % required). Citric acid (50% aq. solution, 6.2 wt. %) is added, followed by triethanolamine (3.45 wt. %). Bio-Soft® EC-690 (laureth-7, 90% actives, 27.8 wt. %, product of Stepan) is slowly added. The pH is adjusted to the 7.8 to 8.4 range, targeting 8.1 with the remaining aqueous sodium hydroxide solution. Sodium xylene sulfonate (40% actives, 4.30 wt. %) is added, followed by a preservative and the remaining deionized water (q.s. to 100 wt. %).

Preparation of an Ultra Laundry Detergent with $C_{16}$ MES and the Blend:

Deionized water (q.s. to 100 wt. %) is charged at 55-60° C. The concentrated blend prepared above (58.0 wt. %) is added while maintaining temperature between 50° C. and 60° C. The $C_{16}$ MES (87% actives, 10.34 wt. %) is slowly added and allowed to dissolve. The mixture is then allowed to cool to 35° C. The experimental sample or cocamide DEA standard (5.0 wt. %) is then added slowly and mixing continues until the batch is homogeneous.

Stability Evaluation:

Ultra laundry detergent samples (about 100 g) are kept at 25° C. or 5° C. for 4 weeks. The samples are monitored for physical changes, including phase separation, gelation, opacification, precipitation, or the like, and the changes are recorded. Results of the evaluation appear in Table 5. Samples that provide at least equal performance in this test are also evaluated for cold-water cleaning performance (see Part B).

As the results show, it is not easy to predict which compositions will have solubility characteristics that are as good or better than cocamide DEA. For instance, C12-17 provides a clear solution even at 5° C., while C10-17, another DMAPA amide, provides a clear solution only at room temperature, similar to cocamide DEA.

It is apparent that an ideal detergent for will have storage stability such that it exhibits a phase transition below 5° C. and will remain clear at 5° C. for a prolonged time period. Of the samples tested, C12-17 meets this criterion, but neither the control nor the other samples do so.

TABLE 5

Storage Stability (4 weeks) of Ultra Laundry Detergents $C_{16}$ MES Formulations; Cocamide DEA standard

| Sample | Appearance, 25° C. | Appearance, 5° C. | Rating |
|---|---|---|---|
| Control | clear | cloudy | — |
| C12-17 | clear | clear | superior |
| C10-17 | clear | cloudy | equal |
| C10-41 | clear | cloudy, thick | equal |
| C10-32 | clear | opaque | equal |
| C10-40 | clear | cloudy | equal |
| C12-30 | clear | cloudy | equal |
| C12-34 | clear | opaque, liquid | equal |
| C12-38 | clear | cloudy | equal |
| C16-9 | clear | opaque paste | equal |
| C16-11 | clear | opaque paste | equal |
| C18-28 | clear | cloudy | equal |
| C18-29 | clear | cloudy | equal |
| C18-30 | clear | cloudy | equal |
| C18-32 | clear | opaque, gel | equal |
| C18-33 | clear | cloudy | equal |
| Mix-37 | clear | opaque, paste | equal |
| C18-38 | clear | opaque, gel | equal |
| Mix-38 | clear | opaque, paste | equal |
| Mix-46 | clear | opaque, paste | equal |
| Mix-61 | clear | opaque | equal |
| C18-68 | clear | cloudy | equal |
| Mix-70 | clear | opaque, gel | equal |
| UTG-11 | clear | opaque | equal |
| UTG-12 | clear | opaque | equal |
| C10-20 | cloudy | not tested | inferior |
| C10-22 | cloudy, gel | cloudy, gel | inferior |
| C12-14 | clear | opaque, solid gel | inferior |
| C12-20 | cloudy, gel | not tested | inferior |
| C18-36 | cloudy | not tested | inferior |
| C18-37 | cloudy, gel | not tested | inferior |

Part B. Cold-Water Cleaning Performance of Compaction Laundry Detergents

This method evaluates the overall cold-water (55° F.) cleaning performance of a laundry detergent formula comprising a concentrated blend of anionic and nonionic surfactants, a builder, $C_{16}$ MES, and an experimental sample. The formulations are prepared as described in Part A, above. The experimental sample is tested for its ability to improve the overall cleaning performance relative to cocamide DEA.

Laundry detergent (30 g, see Part A) is charged to the laundry machine, followed by soiled/stained fabric swatches that are attached to pillowcases. Wash temperature: 55° F. Rinse: 55° F. The swatches are detached from pillowcases, dried, and ironed. Swatches are scanned to measure the L* a* b* values, which are used to calculate a soil removal index (SRI) for each type of swatch. Finally, the ΔSRI is calculated, which equals the experimental sample SRI minus the SRI of a pre-determined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The following standard soiled/stained fabric swatches are used: dust sebum on cotton (DSC); beef tallow (BT); kaolin clay and wool fat on polyester (WFK 30C); grass on cotton (GC); blueberry on cotton (BC); cocoa on cotton (EMPA 112); and blood/ink/milk on cotton (EMPA 116). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L* a* b* values to calculate the SRI for every type of swatch, and the stain removal index (SRI) is calculated as follows:

$$SRI = 100 - \sqrt{(L^*_{clean} - L^*_{washed})^2 + (a^*_{clean} - a^*_{washed})^2 + (b^*_{clean} - b^*_{washed})^2}$$

$$\Delta SRI = SRI_{sample} - SRI_{standard}$$

As shown in Table 6, five of the test samples perform better than cocamide DEA, six samples perform equal to the control, and six samples are inferior when evaluated for cold-water cleaning performance.

The results demonstrate that it is not easy to predict which classes of compounds will provide performance that is at least equal to the control. For instance, even though C12-17 and C10-17 are both DMAPA amides, C12-17 provides superior performance, while C10-17 is rated inferior. In another example, although both C12-30 and C12-38 are both amides from alkanolamines, ethanolamine-based amide C12-30 provides superior performance while the isopropanolamine-based amide C12-38 is rated inferior.

TABLE 6

Performance in Cold-Water Cleaning: |ΔSRI| Values v. Cocamide DEA in a $C_{16}$ Methyl Ester Sulfonate (MES) Formulation *Liquid Formulation*

| | DSC | BT | WFK | GC | BC | 112 | 116 |
|---|---|---|---|---|---|---|---|
| | Superior Performers: | | | | | | |
| C10-41 | −0.6 | 2.5 | −0.3 | −0.6 | 1.6 | 1.2 | 0.3 |
| C12-17 | −0.8 | 5.4 | −0.3 | 0.8 | 1.4 | 1.2 | 0.8 |
| C12-30 | −0.6 | 1.9 | 0.0 | −0.5 | 2.5 | 0.3 | −0.5 |
| C16-11 | 0.4 | 1.1 | 0.5 | −0.6 | 0.3 | 2.0 | 1.6 |
| C18-29 | −0.6 | 1.9 | −0.5 | 0.1 | 2.3 | 1.3 | −0.4 |

TABLE 6-continued

Performance in Cold-Water Cleaning: |ΔSRI| Values v.
Cocamide DEA in a $C_{16}$ Methyl Ester Sulfonate (MES) Formulation
*Liquid Formulation*

|  | DSC | BT | WFK | GC | BC | 112 | 116 |
|---|---|---|---|---|---|---|---|
| Performance Equal to Control Sample: | | | | | | | |
| C16-9 | −0.1 | 1.7 | 0.7 | −1.2 | −0.4 | 1.0 | 0.7 |
| Mix-38 | — | −0.2 | −0.7 | −1.2 | −0.2 | 1.5 | 0.9 |
| Mix-61 | 0.7 | 0.5 | 0.3 | 0.1 | 0.7 | 0.4 | −0.4 |
| Mix-70 | 0.3 | 0.5 | −0.5 | −0.7 | 0.3 | 0.0 | 0.4 |
| UTG-11 | −0.9 | 3.6 | −1.7 | −1.3 | 0.6 | −0.3 | −0.4 |
| UTG-12 | −0.6 | −0.3 | 0.2 | −0.5 | −0.2 | 0.0 | −0.7 |
| Inferior Performers: | | | | | | | |
| C10-17 | −0.7 | −1.8 | −0.5 | −0.1 | 1.5 | 1.6 | −0.5 |
| C12-34 | −0.4 | −3.3 | 0.1 | 0.2 | 0.4 | −0.2 | −0.7 |
| C12-38 | −0.5 | −1.8 | 0.4 | 1.1 | 0.8 | −0.5 | 0.0 |
| C18-30 | −0.7 | 0.0 | −0.9 | −1.2 | 1.6 | 0.7 | −0.2 |
| C18-32 | −0.3 | −0.1 | −1.1 | 0.2 | 2.1 | 1.1 | −1.3 |
| C18-38 | −0.8 | 2.0 | −2.0 | −2.0 | 1.6 | 0.1 | −1.1 |

Part C. Booster for Bargain Laundry Detergent

This method evaluates the cleaning boosting ability of an experimental sample when used as an additive in a bargain laundry detergent formulation that contains neutralized dodecylbenzene sulfonic acid, a non-ionic surfactant such as an ethoxylated synthetic $C_{12}$-$C_{15}$ alcohol (7 EO), citric acid, monoethanolamine, triethanolamine, and a preservative. The experimental sample is tested for its ability to improve the overall cleaning performance at 1% solids level relative to Ammonyx® LO (lauramine oxide, standard booster, product of Stepan). Laundry detergent formula (46 g) is charged to the laundry machine, followed by soiled/stained fabric swatches that are attached to pillowcases. Wash temperature: 90° F. Rinse: 70° F. The swatches are detached from pillowcases, dried, and ironed.

The bargain laundry detergent with booster is prepared from sodium hydroxide-neutralized dodecylbenzene sulfonic acid (Bio-Soft®S-101, 33.9% actives, 41.3 wt. %), Bio-Soft® N25-7 (fatty alcohol ethoxylate, product of Stepan, 5.00 wt. %), booster (either the experimental sample or Ammonyx LO, which is 30% actives, 3.33 wt. %, citric acid (50% aq. solution, 1.00 wt. %), monoethanolamine (1.00 wt. %), triethanolamine (1.00 wt. %), and deionized water plus preservative (balance to 100 wt. %).

The formulation is made by charging 90% of the total amount of water at 50° C., then adding in order, with mixing, citric acid solution, monoethanolamine, triethanolamine, neutralized sulfonic acid, Bio-Soft N25-7, and booster. The pH is adjusted to 9.5 with 25% aq. NaOH solution, and then preservative and the balance of the water are added.

The following standard soiled/stained fabric swatches are used: dust sebum on cotton (DSC); dust sebum on cotton/polyester (DSCP); beef tallow (BT); clay on cotton (CC); clay on cotton/polyester (CCP); grass on cotton (GC); red wine on cotton (RWC); blueberry on cotton (BC); coffee on cotton (COFC); cocoa on cotton (EMPA 112); blood/ink/milk on cotton (EMPA 116); and make-up on cotton (EMPA 143). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L* a* b* values to calculate the SRI for every type of swatch, and the stain removal index (SRI) is calculated as described in Part B.

As shown in Table 7, three of the test samples perform as well as the control, one is superior, and seventeen samples are inferior when evaluated as boosters for bargain laundry detergents. The results demonstrate that it is not easy to predict which classes of compounds will provide performance that is at least equal to the control.

TABLE 7

Performance as a Booster for a Bargain Detergent Formulation: |ΔSRI|
Values versus Ammonyx LO (Lauramine Oxide)

|  | DSC | DSCP | BT | CC | CCP | GC | RWC | BC | COFC | 112 | 116 | 143 |
|---|---|---|---|---|---|---|---|---|---|---|---|---|
| Performance Superior to Control Sample: | | | | | | | | | | | | |
| Mix-46 | 0.9 | 1.4 | −0.3 | 0.7 | 0.4 | 1.0 | 1.6 | 0.1 | −0.4 | −0.5 | 0.7 | −0.2 |
| Performance Equal to Control Sample: | | | | | | | | | | | | |
| C12-33 | 0.7 | 0.9 | −0.7 | 0.8 | −0.3 | −1.6 | −0.3 | −0.9 | −0.5 | 0.5 | 0.3 | 0.2 |
| Mix-73 | 1.0 | 0.3 | −2.9 | 0.0 | 1.0 | 1.0 | 1.0 | 0.2 | −0.2 | 0.1 | 1.2 | 1.2 |
| PMTG-11 | 0.5 | 0.9 | −0.7 | −0.2 | −0.4 | −0.6 | −0.1 | −0.9 | −0.6 | 0.5 | 0.1 | 0.0 |
| Inferior Performers: | | | | | | | | | | | | |
| C10-18 | −1.1 | 0.7 | — | −1.1 | −0.8 | — | 0.8 | — | — | 1.6 | — | — |
| C10-19 | −2.2 | 1.1 | — | −1.7 | 0.9 | — | 0.7 | — | — | 0.2 | — | — |
| C10-20 | −1.0 | −1.1 | — | 0.4 | −0.2 | — | 0.5 | — | — | 0.4 | — | — |
| C10-21 | −1.1 | −1.0 | — | −1.0 | −0.3 | — | 1.0 | — | — | 0.1 | — | — |
| C10-22 | −3.0 | 0.8 | — | −1.0 | 0.8 | — | −0.2 | — | — | 0.5 | — | — |
| C12-24 | −0.2 | −0.8 | — | −1.0 | −0.3 | — | 1.1 | — | — | −1.5 | — | — |
| C10-25 | −1.7 | 1.4 | — | 0.5 | 1.1 | — | 0.6 | — | — | −0.1 | — | — |
| C12-14 | 0.6 | 0.7 | −1.6 | −0.2 | −0.3 | −0.7 | 0.1 | −1.2 | −0.8 | 0.5 | 0.2 | −0.1 |
| C12-19 | 1.0 | 1.5 | −9.9 | 0.1 | 0.1 | 0.4 | 0.0 | 0.0 | 0.3 | 1.6 | 0.0 | 0.2 |
| C12-20 | −0.6 | −1.1 | — | −2.3 | −0.7 | — | 0.7 | — | — | −1.5 | — | — |
| C18-28 | 0.6 | 1.4 | −11 | −0.3 | −0.8 | 1.8 | −0.5 | −0.7 | −1.2 | 0.8 | −0.3 | −0.5 |
| C18-33 | −0.5 | 0.1 | −19 | −0.7 | −1.6 | 0.3 | −3.4 | −5.4 | −1.9 | −1.8 | 0.2 | −0.4 |
| C18-34 | 0.6 | 1.6 | −8.5 | −0.2 | −0.4 | 1.3 | −0.8 | 0.5 | −0.8 | 0.3 | 0.9 | −0.1 |
| C18-36 | −0.2 | 2.1 | −12 | −0.3 | −0.3 | 0.3 | 0.4 | −0.2 | −0.5 | 1.3 | −0.1 | 0.0 |
| C18-37 | 0.5 | 2.1 | −11 | 0.0 | −0.2 | 0.3 | 0.0 | −0.2 | −0.6 | 0.1 | 1.4 | −0.1 |

TABLE 7-continued

Performance as a Booster for a Bargain Detergent Formulation: |ΔSRI|
Values versus Ammonyx LO (Lauramine Oxide)

|  | DSC | DSCP | BT | CC | CCP | GC | RWC | BC | COFC | 112 | 116 | 143 |
|---|---|---|---|---|---|---|---|---|---|---|---|---|
| C18-68 | 0.2 | 0.9 | −11 | −0.2 | −0.4 | 1.0 | −0.5 | −1.5 | −1.2 | 0.0 | −0.3 | 0.0 |
| MTG-6 | −2.1 | 0.3 | — | −1.4 | 0.4 | — | −0.8 | — | — | −0.4 | — | — |

Part D. Cold-Water Cleaning Performance of a Powder Detergent Formulation

Amidoamine C12-17 is tested as an additive in a $C_{16}$ MES-based powder-like laundry detergent formulation to evaluate cold-water cleaning performance relative to cocamide DEA, an industry standard.

Formulation:

Solid phase components: $C_{16}$ MES (10.34 g, 87% actives); sodium chloride (38.6 g), sodium silicate (19.3 g), sodium carbonate (9.60 g).

Liquid phase components: linear alkylbenzene sulfonate (NaLAS, 2.95 g, 33.9% actives); Bio-Soft® N25-7 (17.5 g), amidoamine C12-17 (5.00 g, 100% actives).

The solid phase components are mixed first, and the liquid phase components are then combined with the solids and mixed by hand until homogeneous.

Detergent dosage is determined by the amount of $C_{16}$ MES previously dosed with the compaction liquid laundry detergent formula. For the liquid detergent, 30 g of 9% actives MES was used to give 2.7 g in the wash liquor. Therefore, the dose of powder formula needed is 2.7×100/8.71=31 g.

The powder detergent is used to wash standard stained/soiled swatches at 55° F. as has been previously described in the cold water cleaning section (Part B). Results appear in Table 8. As the results show, C12-17 provides superior performance relative to cocamide DEA when used as in a powder form.

TABLE 8

Performance in Cold-Water Cleaning:
|ΔSRI| Values v. Cocamide DEA in a
$C_{16}$ Methyl Ester Sulfonate (MES) Formulation
*Powder Formulation*

|  | DSC | BT | WFK | GC | BC | 112 | 116 |
|---|---|---|---|---|---|---|---|
| Superior Performers: | | | | | | | |
| C12-17 | 1.00 | 2.12 | 0.56 | 1.55 | 0.41 | −0.32 | −0.36 |

The preceding examples are meant only as illustrations. The following claims define the invention.

We claim:

1. A laundry detergent useful for cold-water cleaning, comprising 1 to 70 wt. % of an anionic surfactant, 5 to 70 wt. % of a nonionic surfactant, 3 to 25 wt. % of a fatty alkyl ester sulfonate, and 0.5 to 10 wt. % of a metathesis-based surfactant composition selected from the group consisting of (a) a $C_{10}$ betaine having the structure:

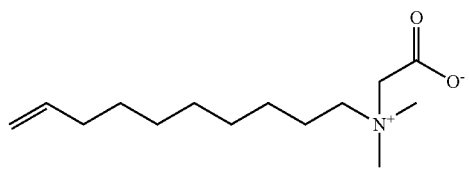 [SMILES: C=CCCCCCCCC[N+](C)(C)CC(=O)[O-]]

(b) a $C_{12}$ or $C_{16}$ amidoamine having the structure:

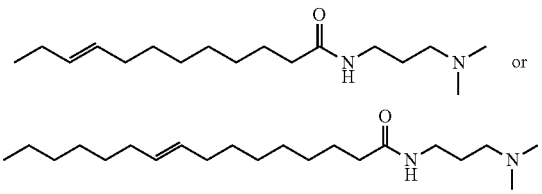

(c) a $C_{12}$ ethanolamine amide having the structure:

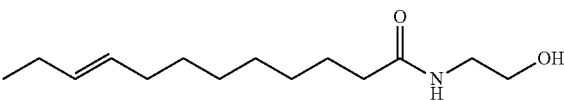 [SMILES: CC/C=C/CCCCCCCC(=O)NCCO]

(d) a $C_{16}$ amidoamine sulfonate having the structure:

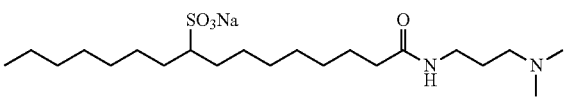

(e) a $C_{18}$ diamidoamine dioxide having the structure:

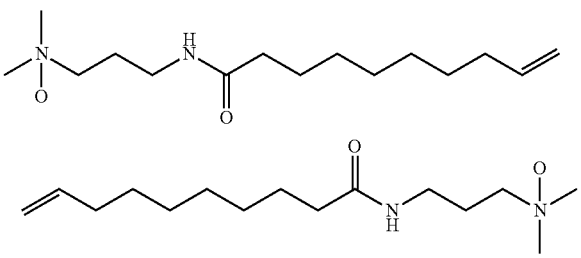

(f) a quaternized C₁₈ diamidoamine betaine having the structure:

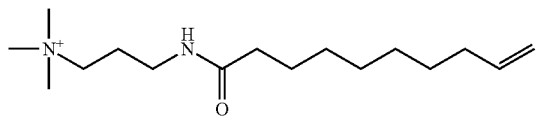

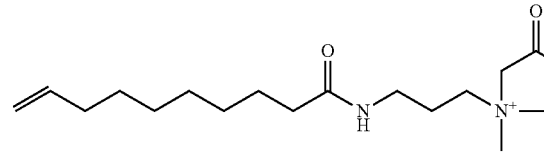

(g) a sulfonated $C_{18}$ low-EO fatty ester alkoxylates having the structure:

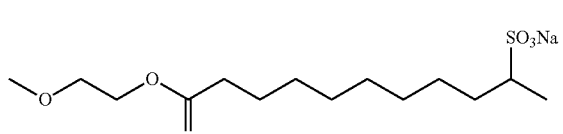

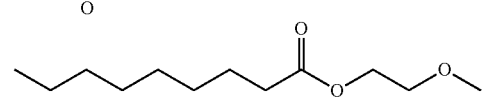

(h) a $C_{18}$ amidoamine carboxylate having the structure:

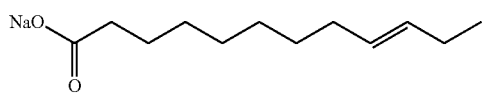

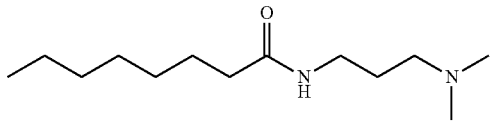

(i) an amidoamine oxide derived from cross-metathesis of palm or soybean oil having the structure:

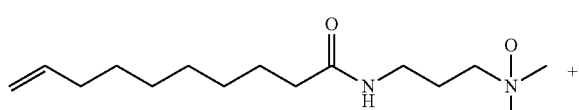

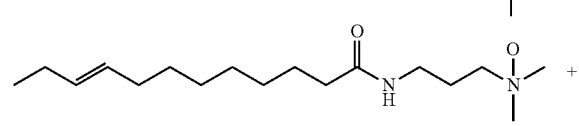

-continued

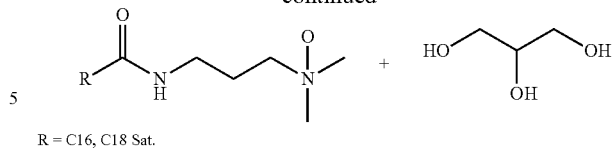

R = C16, C18 Sat.

and (j) a sulfobetaine derived from cross-metathesis of palm or soybean oil having the structure:

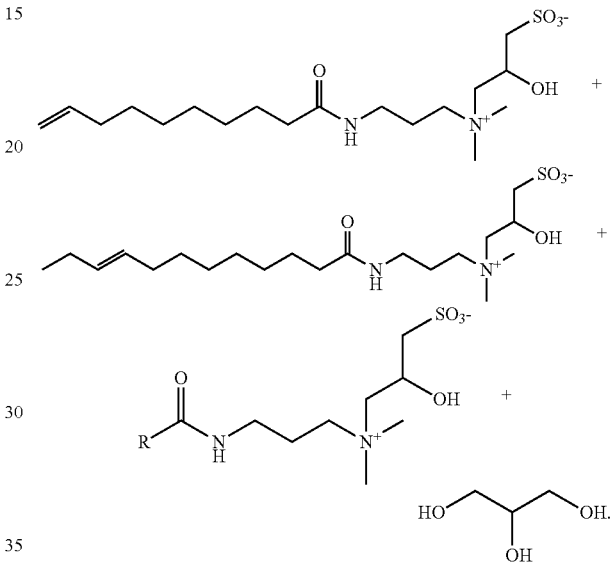

R = C16, C18 Sat.

2. The detergent of claim 1 wherein the nonionic surfactant is a fatty alcohol ethoxylate.

3. The detergent of claim 1 wherein the acid or ester metathesis-based surfactant composition has at least 1 mole % of trans-$\Delta^9$ unsaturation.

4. A liquid, powder, paste, granule, tablet, molded solid, water-soluble sheet, or water-soluble sachet comprising the detergent of claim 1.

5. The detergent of claim 1 further comprising water.

6. A storage-stable liquid detergent of claim 5.

7. The detergent of claim 1 that is a liquid at 20° C. and exhibits a phase transition below 5° C.

* * * * *